United States Patent
Warenius et al.

(12)

(10) Patent No.: US 6,521,407 B1
(45) Date of Patent: Feb. 18, 2003

(54) METHODS FOR DETERMINING CHEMOSENSITIVITY OF CANCER CELLS BASED UPON EXPRESSION OF NEGATIVE AND POSITIVE SIGNAL TRANSDUCTION FACTORS

(75) Inventors: Hilmar Meek Warenius, Wirral (GB); Laurence Anthony Seabra, Wirral (GB)

(73) Assignee: TheRyte Limited, Liverpool (GB)

( * ) Notice: Subject to any disclaimer, the term of this patent is extended or adjusted under 35 U.S.C. 154(b) by 0 days.

(21) Appl. No.: 09/622,277

(22) PCT Filed: Feb. 18, 1999

(86) PCT No.: PCT/GB99/00500
§ 371 (c)(1),
(2), (4) Date: Oct. 25, 2000

(87) PCT Pub. No.: WO99/42834
PCT Pub. Date: Aug. 26, 1999

(30) Foreign Application Priority Data

| | | | |
|---|---|---|---|
| Feb. 18, 1998 | (GB) | ............................................. | 9803446 |
| Feb. 18, 1998 | (GB) | ............................................. | 9803447 |
| Jun. 5, 1998 | (GB) | ............................................. | 9812151 |
| Jul. 3, 1998 | (GB) | ............................................. | 9814545 |
| Feb. 10, 1999 | (GB) | ............................................. | 9903035 |

(51) Int. Cl.[7] ............................................. C12Q 1/68
(52) U.S. Cl. ....................................................... 435/6
(58) Field of Search ............................................. 435/6

(56) References Cited

U.S. PATENT DOCUMENTS 5,381,224 A * 1/1995 Dixon et al. .................. 356/72

FOREIGN PATENT DOCUMENTS

WO    WO 97/04316    * 2/1997

OTHER PUBLICATIONS

Riva, C. et al., "Differential c–myc, c–jun, c–raf and p53 Expression in Squamous Cell Carcinoma of the Head and Neck: Implication in Drug and Radioresistance", Oral Oncol. Eur. J. Cancer, vol. 31B, pp. 384–391 (1995).*

Tanke, H. J. et al., "Selection of defined cell types by flow–cytometric cell sorting", Trends in Biotech., vol. 11, pp. 55–62 (1993).*

* cited by examiner

Primary Examiner—Gary Benzion
Assistant Examiner—Teresa Strzelecka
(74) Attorney, Agent, or Firm—Rothwell, Figg, Ernst, Manbeck, P.C.

(57) ABSTRACT

Provided is a method for measuring the sensitivity of a cancer cell to an anticancer agent, which method comprises testing a sample for the mutational status, expression, and/or function of a negative signal transduction factor (NSTF), and testing the sample for the mutational status, expression, and/or function of a positive signal transduction factor (PSTF), wherein when the method comprises measuring the radiosensitivity of wild-type p53 cancer cells by testing a sample comprising wild-type p53 cells or an extract therefrom for the abundance of Raf-1 protein by Western blotting, an antibody specific to Raf-1 protein is employed.

12 Claims, 7 Drawing Sheets

Wild Type p53

Mutant p53

UNDETECTABLE p21

HIGH p21 p53 mutants p53 wild-type

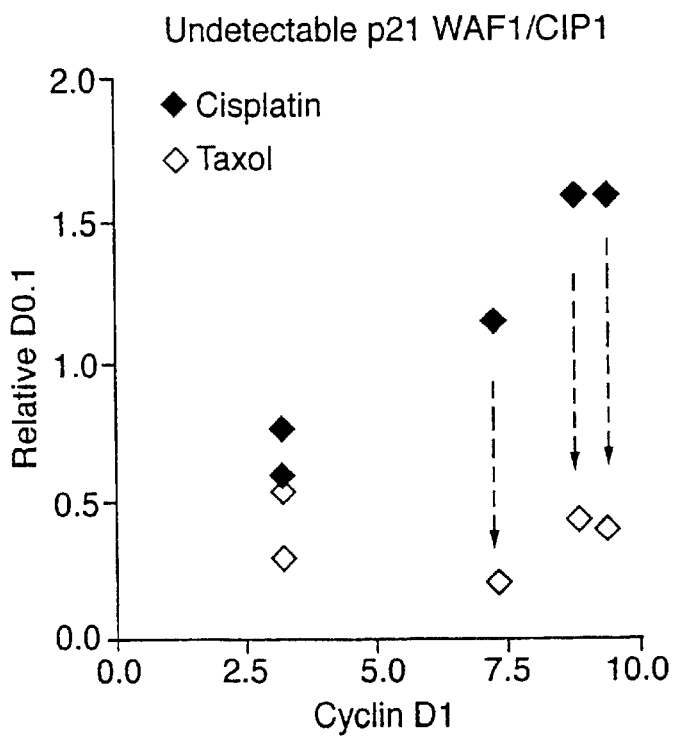
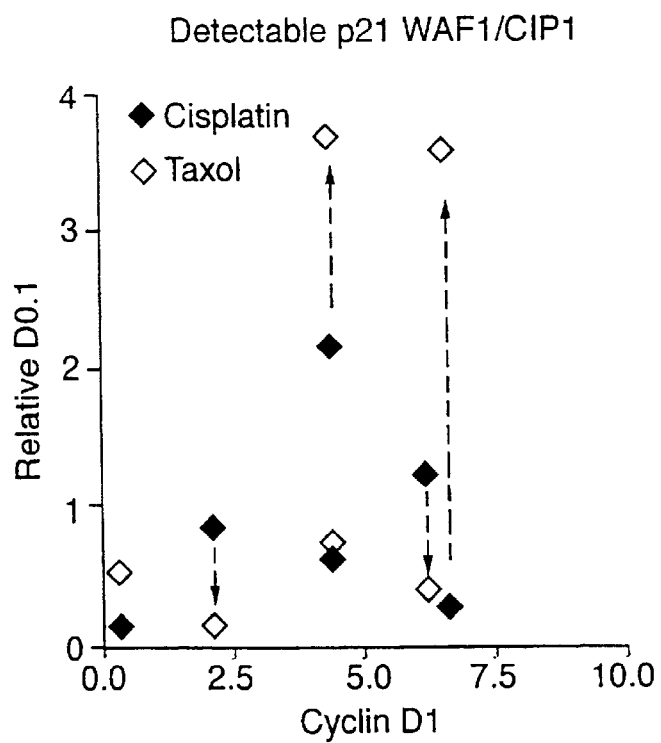

METHODS FOR DETERMINING CHEMOSENSITIVITY OF CANCER CELLS BASED UPON EXPRESSION OF NEGATIVE AND POSITIVE SIGNAL TRANSDUCTION FACTORS

The present application concerns methods of selecting the most appropriate therapy for patients suffering from cancer. The application is particularly concerned with measuring the resistance of cancer cells to anti-cancer agents.

Although radiotherapy and chemotherapy have been responsible for curing many people of cancer in the latter half of this century, there still remain a large number of tumours which either show little response to treatment, or respond initially only to recur later. In particular, women treated for ovarian cancer with platinating agents often show encouraging initial responses to chemotherapy (which often involves the use of cis-diamminedichloroplatinum (CDDP) as the drug of first choice), but by 5 years after diagnosis, ⅔ of them have succumbed to their disease. Similarly lung cancer patients may respond favourably to combination chemotherapy regimens containing CDDP at the outset of treatment but very few experience long term survival. A better understanding of the mechanisms underlying the responsiveness of cancers to CDDP could help predict which patients are most likely to benefit from CDDP or whether alternative cytotoxic agents such as taxol or different therapies such as radiotherapy might be appropriate. Understanding treatment response mechanisms also holds the possibility of selectively modulating these mechanisms to improve the treatment of human cancer using, for example, CDDP.

It has become increasingly apparent that certain oncogenes and tumour suppressor genes may not only be implicated in carcinogenesis, but can also influence the sensitivity of malignant cells to therapeutic agents. Attempts have therefore been made to use these and other genes to try and predict the therapeutic response of human cancer to the presently available treatment modalities such as radiotherapy and/or cytotoxic chemotherapy. Research up to the present time, however, has generally attempted to only examine the expression of single tumour related genes as methods of predicting therapeutic response. Research in the public domain has suggested that mutations in the p53 tumour suppressor gene, which can be found in around 50% of common cancers such as those of the breast, lung and ovary, are associated with resistance to treatment with cytotoxic drugs or radiation. Despite a considerable body of work, however, there are at present no successful clinical tests by which the detection of mutations in the p53 gene alone can be used to predict with an acceptable degree of certainty whether or not a patients cancer is likely to respond to chemotherapy with, for example, platinating agents or the newer cytotoxic agents such as taxanes (e.g. Paclitaxel (TAXOL)).

The effect of the expression of single genes alone on the response of human cancer cell lines to treatment with cytotoxic drugs such as CDDP (cisdiamminedichloroplatinum) has been studied in human in vitro cell lines because these present a model system relevant to the response of human cancer in the clinic. In particular, they exhibit the range of sensitivities to cytotoxic drugs and ionising radiation usually encountered in the clinic. Discoveries in human in vitro cell lines, therefore, have a strong possibility of being able to be translated into clinically useful tests for how well cancers may be expected to respond to treatment.

The progress of cells through the cell cycle is governed by holoenzymes formed by a combination of proteins called cyclins, whose levels fluctuate throughout the cell cycle, and cyclin dependent kinases (CDKs) which become active when they join with cyclins. The cyclin/CDK complexes can be inhibited by proteins termed cyclin dependent kinase inhibitors (CDKIs) which include the protein p21 WAF1/CIP1 (p21).

The protein products of the cyclin D1 and B1 genes and their respective cyclin-dependent kinase partners CDK4 and CDK1 have been studied. Cyclin D1 and CDK4 control the progress of cells through the cell cycle checkpoint between G1 and S-phase (the phase of DNA synthesis). Cyclin B1 and CDK1 control the cell cycle checkpoint just before mitosis. The expression of cyclin D1 protein in a series of 16 human cancer cell lines has been shown to be related to their intrinsic resistance to the cytotoxic drug CDDP (Warenius et al., 1996). Cyclin D1 protein levels, however, showed no relationship with radiosensitivity, another treatment modality. The relationship between cyclin D1 and CDDP resistance is not, however, strong enough on its own to provide the basis of clinically useful predictive assays.

Paclitaxel, which is a member of the class of anti-cancer drugs known as taxanes, has been shown clinically to be of benefit when added to treatment with platinating agents in the clinical treatment of ovarian cancer. It has been reported that cells can become more sensitive to Paclitaxel when they lose normal p53 function as a result of infection with human papilloma virus constructs or SV40 virus constructs (Wahl et al, Nature Medicine, vol. 2, No. 1, 72–79, 1996). This is thought to result from increasing G2/M arrest and apoptosis. However, it is not the case that all p53 mutant cancer cells are sensitive to Paclitaxel (TAXOL). Accordingly, based on this correlation on its own these studies have not been able to engender a reliable predictive method for determining a likely effective treatment in specific cases.

Thus, there are no indicators that measuring the mutational status or levels of expression of the protein products of single oncogenes, proto-oncogenes or tumour suppressor genes in human cancer cells would be able to provide the basis of a reliable clinical test for whether clinical tumours were likely to respond to treatment with chemotherapeutic agents, including platinating agents and CDDP.

Although radiotherapy has been responsible for curing many people of cancer in the latter half of this century, there still remain a large number of tumours which either show little response to treatment, or respond initially only to recur later. A better understanding of the mechanisms underlying the responsiveness of cancers to radiotherapy could help predict which patients are most likely to benefit from radiotherapy, and also holds the possibility of selectively modulating these mechanisms to improve the treatment of human cancer using radiotherapy.

The molecular basis of intrinsic radiosensitivity has been under investigation for many years. A considerable body of research has focused on the degree of DNA damage and its subsequent repair as reflected in the incidence of double strand breaks (dsbs) in the DNA (Kelland et al, 1988; Schwartz et al, 1991), the residual damage remaining in the DNA after cellular rejoining of dsbs (Nunez et al, 1995; Whitaker et al, 1995), and the fidelity of DNA repair (Powell & McMillan, 1994). In addition to DNA damage, however, it has become increasingly apparent that certain oncogenes and tumour suppressor genes may not only be implicated in carcinogenesis, but can also influence the sensitivity of malignant cells to ionising radiation.

As a result of this growing evidence of the role of oncogenes and tumour suppressor genes in the sensitivity of malignant cells to therapeutic agents, attempts have been made to use these and other genes to try and predict the therapeutic response of human cancer to the presently available treatment modalities such as radiotherapy and/or cytotoxic chemotherapy. Research up to the present time, however, has generally attempted to only examine the expression of single tumour related genes as methods of predicting therapeutic response. When investigating the relationship between expression of a chosen gene and intrinsic radiosensitivity, consideration has not necessarily been given as to whether other candidate genes than the one selected for study might also have an affect on the outcome of experiments.

Research into the role of individual genes has focused on a number of cell cycle genes and signal transduction genes. Transfection of normal cell lines with dominant oncogenes such as myc and ras (McKenna et al, 1991) has resulted in increased radioresistance even in the absence of detectable changes in the rate of dsb induction (Iliakis et al, 1990). Several other dominant oncogenes including c-fms, v-sis, v-erb-B, v-abl, v-src, v-cot (Fitzgerald et al 1990, Suzuki et al, 1992, Shimm et al, 1992) and c-Raf (Kasid et al, 1989, Pirollo et al, 1989) have also been reported to modulate cellular radiosensitivity in mammalian cells. The potential relevance of these findings to clinical radiotherapy has been emphasised by observations that high levels of Raf-1 (the normal protein product of the c-Raf-1 proto-oncogene) are related to intrinsic radiosensitivity in human in vitro cell lines (Warenius et al, 1994). However, these results are not sufficient alone to determine the sensitivity of a tumour to radiotherapy in a clinical assay.

An additional body of evidence indicates a positive relationship between mutation in the p53 tumour suppressor gene and increased cellular radioresistance in both rodent and human tumour cells (Fan et al, 1994, Radford 1994, Zhen et al, 1995, Xia et al, 1995, Lee and Bernstein 1993) and in normal cells transfected with mutant p53 (mp53) genes (Pardo et al, 1994, Bristow et al, 1994, Kawashima et al, 1995). Research in the public domain has suggested that mutations in the p53 tumour suppressor gene, which can be found in around 50% of common cancers such as those of the breast, lung and ovary, are associated with resistance to treatment with cytotoxic drugs or radiation. Despite a considerable body of work, however, there are at present no successful clinical tests by which the detection of mutations in the p53 gene alone can be used to predict with an acceptable degree of certainty whether or not a patient's cancer is likely to respond to radiotherapy. A wide disparity of results in clinico-pathological studies comparing tumour response and p53 status leads to the conclusion that at the present time p53 mutation or the over-expression of p53 protein are not sufficient alone to predict whether or not a human cancer is likely to respond to radiotherapy.

A number of reports suggest that oncogenes and suppressor genes may modulate intrinsic radiosensitivity by their influence on the progress of irradiated cells through radiation-induced blocks at cell cycle checkpoints. G1/S delay, mediated by p53 following exposure to ionising radiation has been implicated as an important measure of cell cycle perturbation which correlates with relative radiation sensitivity (Kastan et al, 1991, McIlwrath et al, 1994; Siles et al, 1996). Also, the expression of dominant oncogenes such as myc and ras (McKenna et al, 1991) or SV40 (Su & Little, 1993) has been shown to induce both radioresistance and a concomitant increase in post-radiation delay at the G2/M checkpoint. It has also been shown that the protein product of the normal c-Raf-1 proto-oncogene was related to radiosensitivity in 19 human in vitro cell lines (Warenius et al, 1994). Recently, it has further been shown that in 6 of the above 19 cell lines, the previously observed Raf-1/radiosensitivity relationship was very strong and related to how rapidly cells exited from a radiation-induced block at the G2/M cell cycle checkpoint. Those radiosensitive human cancer cells with increased expression of the normal Raf-1 protein exhibit more rapid exit from a G2/M block induced by 2Gy of radiation than radioresistant cells with low expression of Raf-1 (Warenius et al, 1996). High expression of the Raf-1 protein product of the normal c-Raf proto-oncogene is related to radiosensitivity but has no relationship with resistance to CDDP. The relationship between Raf-1 and radiosensitivity is not, however, strong enough on its own to provide the basis of clinically useful predictive assays. The same is true of other attempts to correlate the effects of single genes to the success of therapies.

Unfortunately, little is known about whether, or how, oncogenes and suppressor genes may interact to influence the radiosensitivity phenotype of human cancer cells. However, transfection experiments using cells from other mammals, such as REF (rat embryo fibroblasts), have demonstrated greater increases in radioresistance in cells expressing dominant plus co-operating oncogenes than expressing the single dominant oncogenes alone (McKenna et al, 1990, Su & Little 1992, Pirollo et al, 1993). Similarly, radioresistance induced in REF cells by transfection with multiply integrated mutant p53-pro193 alleles was much greater when the mutant p53 gene was co-transfected with H-ras (Bristow et al, 1994).

It has been shown more recently (Warenius et al, 1994, 1996) that measuring Raf-1 protein in the context of wild-type p53 provides a correlation which could possibly provide the basis of a predictive assay for radiosensitivity. This relationship was demonstrated by measuring Raf-1 protein using quantitative Western blotting. Western blotting is, however, expensive, time consuming and laborious. Furthermore, it requires large numbers of cells. It is thus impractical as a routine clinical test in this particular case. A clinical assay is preferably capable of measuring protein levels in individual cells, rather than in homogenates of a million or more cells as used in Western blotting. It is also important to be able to distinguish Raf protein expression in tumour cells from that in normal cells. This requires the ability to gate out cells on the basis that they are diploid rather than aneuploid in flow cytometry assays, or the ability to measure Raf protein in individual cells that can be observed histologically on tissue sections where morphological criteria enable regions of tumour to be distinguished from connective tissue, blood vessels infiltrating white blood cells, or area of necrosis.

Unfortunately all available antibodies against Raf cross-react with an irrelevant epitope on a 48 kD molecule, when examined on Western blots (see FIG. 3). Raf-1 is a 72–74 kD molecule and can thus be distinguished and separately measured on Western blotting. Cellular assays for Raf-1 such as flow cytometry or immunocytochemistry would rot, however, be able to distinguish the correct 72–74 kD molecule from the irrelevant 48 kD molecule. The 48 kD protein is unlikely to be a fragment of the 72 kD Raf proto-oncogene because the 48 kD protein is much more abundant than the 72 kD protein on Western blotting.

Thus, on the basis of the above state of the art, at the present time there are no indicators that measuring the mutational status or levels of expression of the protein products of oncogenes, proto-oncogenes or tumour suppressor genes in human cancer cells would be able to provide the basis of a reliable clinical test for whether clinical tumours were likely to respond to drug and/or radiation treatment.

An object of the present invention is to solve the above problems. Accordingly, this invention provides a method for measuring the sensitivity of a cancer cell to an anti-cancer agent, which method comprises testing a sample for the mutational status, expression, and/or function of a negative signal transduction factor (NSTF), and testing the sample for the mutational status, expression, and/or function of a positive signal transduction factor (PSTF), wherein when the method comprises measuring the radiosensitivity of wild-type p53 cancer cells by testing a sample comprising wild-type p53 cells or an extract therefrom for the abundance of Raf-1 protein by Western blotting, an antibody specific to Raf-1 protein is employed.

In the context of this invention a factor includes any gene, molecule, component or product, and in particular such factors which are contained in cells. The steps of testing for the NSTF and testing for the PSTF can be carried out in any order.

Also in the context of the present invention, a NSTF is intended to include a factor which inhibits or arrests the cell cycle, causes cells to withdraw from the cell cycle, and/or causes apoptosis or other cell death thereby inhibiting cell division. Thus the NSTF may be a suppressor and/or a PSTF inhibitor. Examples of NSTFs include p53 (in particular its mutational status), p21 (in particular the level of expression of p21 and/or the abundance of p21 protein), Raf-1 inhibitors, cyclin D1 inhibitors and cyclin dependent kinase inhibitors such as CDK1 inhibitors and CDK4 inhibitors.

References to PSTFs in the present invention are intended to include a transcription factor, an oncogene, a proto-oncogene, a gene which inhibits and/or controls cell cycle division, and/or a cell surface receptor. Thus, PSTFs include Raf-1 (in particular the level of expression of Raf-1 and/or the abundance of Raf-1 protein), cyclin D1 (in particular the level of expression of Cyclin D1 and/or the abundance of Cyclin D1 protein) or a cyclin dependent kinase such as CDK1 or CDK4 (in particular the abundance of such cyclin dependent kinases).

This invention also provides a kit for measuring the sensitivity of a cancer cell to an anti-cancer agent, which kit comprises:
  (i) a means for testing a sample for the mutational status, expression, and/or function of a negative signal transduction factor (NSTF), and
  (ii) a means for testing a sample for the mutational status, expression, and/or function of a positive signal transduction factor (PSTF).

The present invention will be described in further detail by way of example only with reference to the accompanying drawings, in which.

Figure 3:
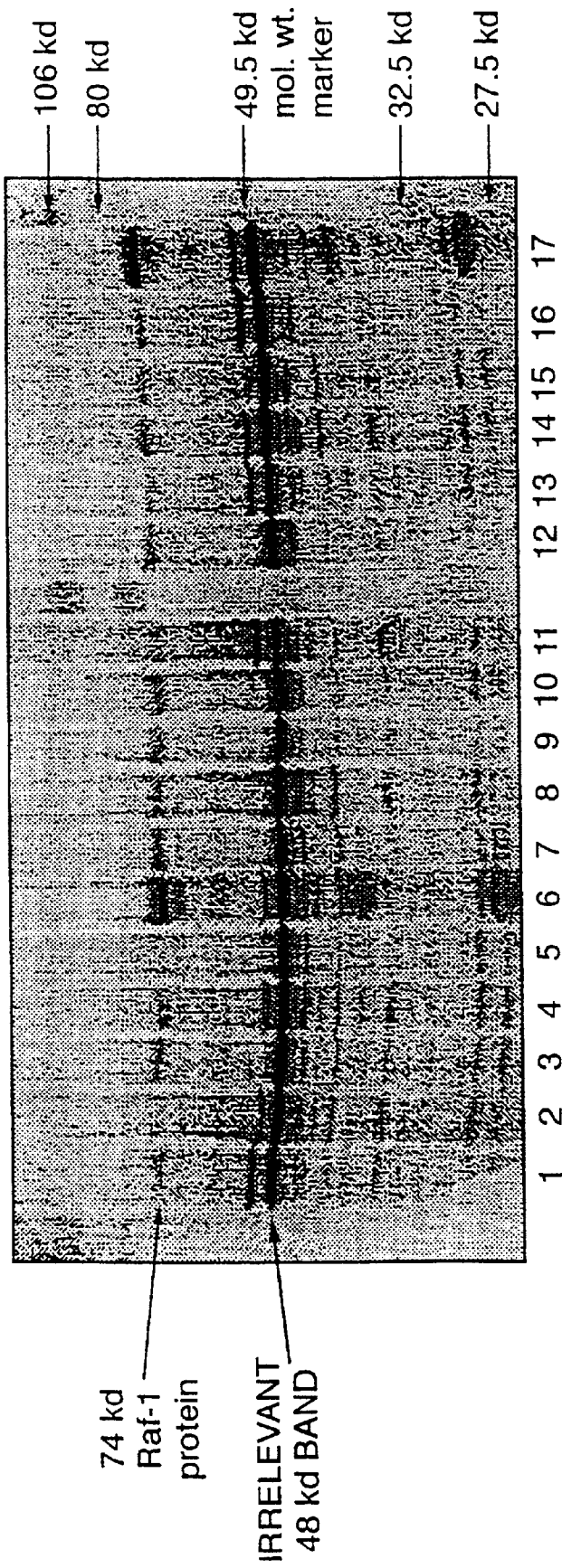
Figure 4:
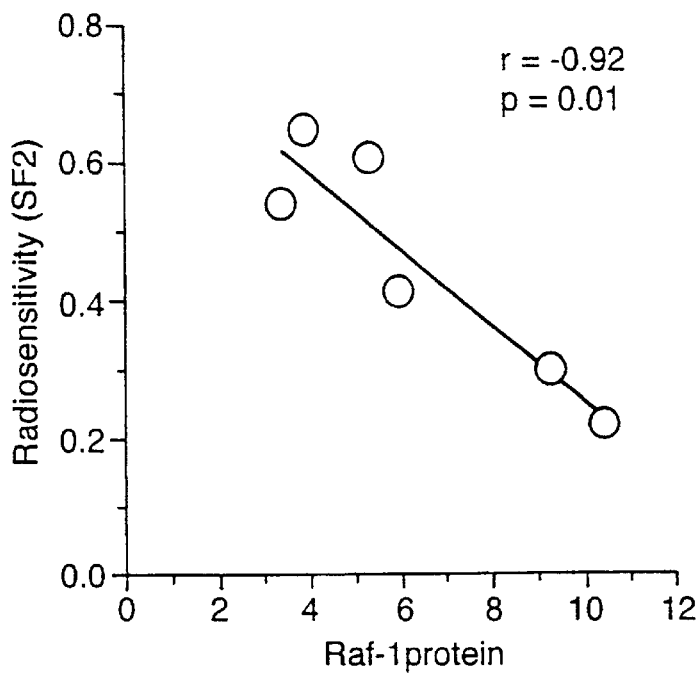
Figure 5:
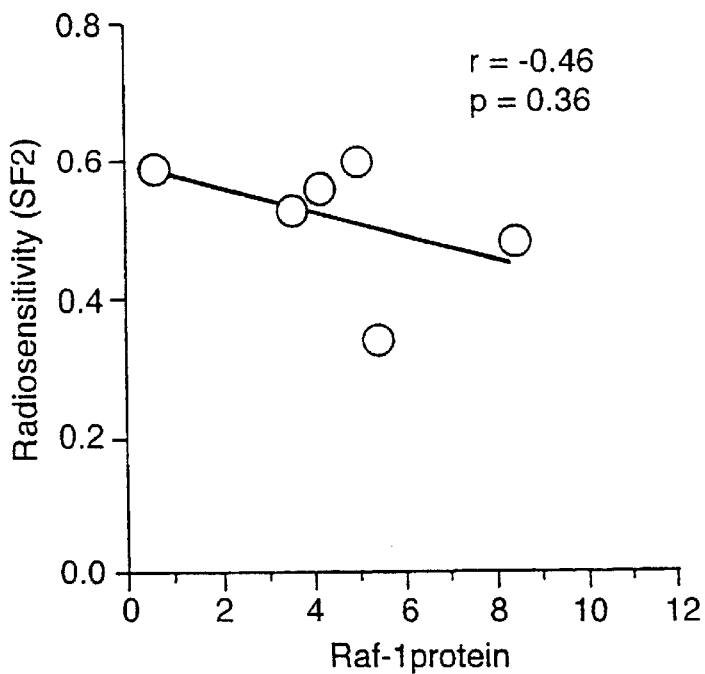
Figure 6:
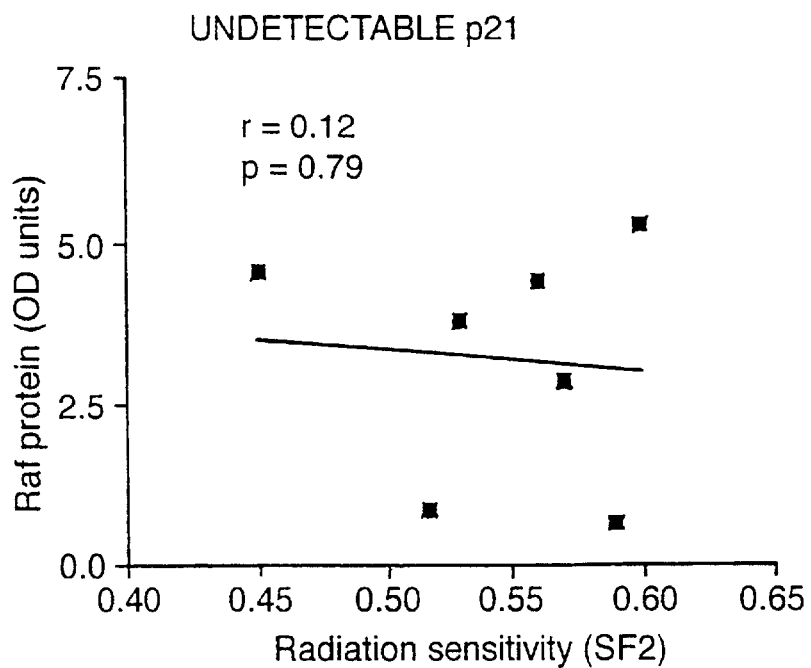
Figure 7:
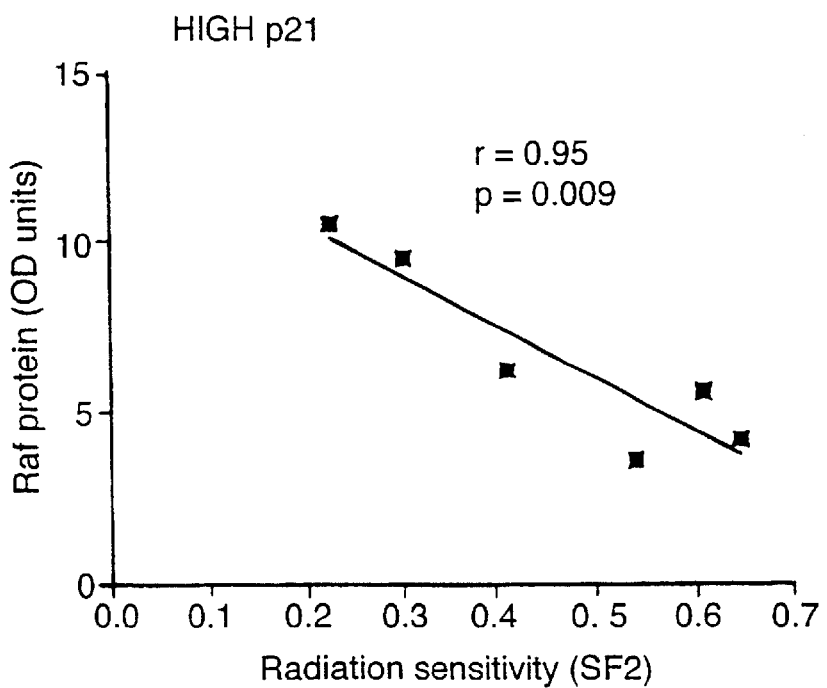
Figure 8:
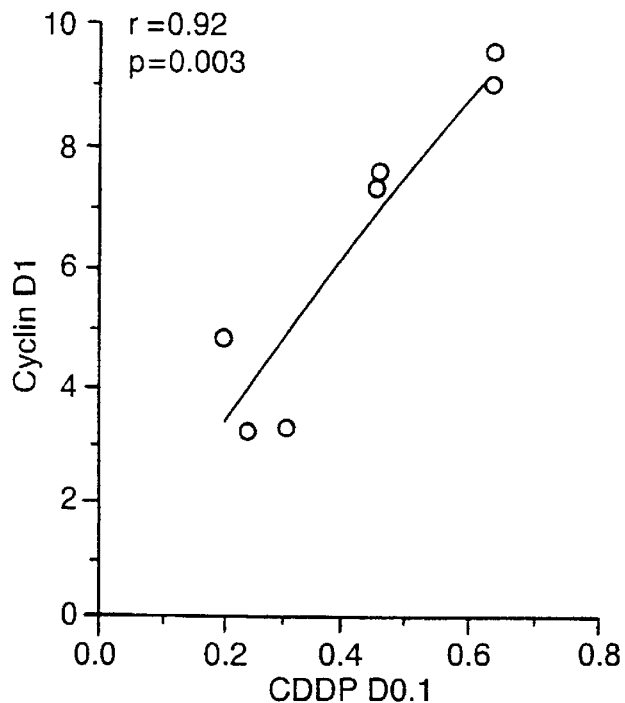
Figure 9:
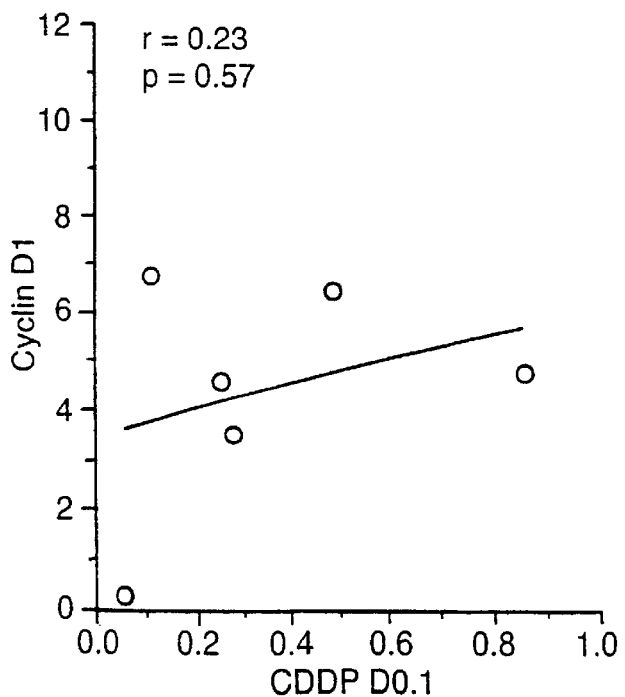
Figure 10:
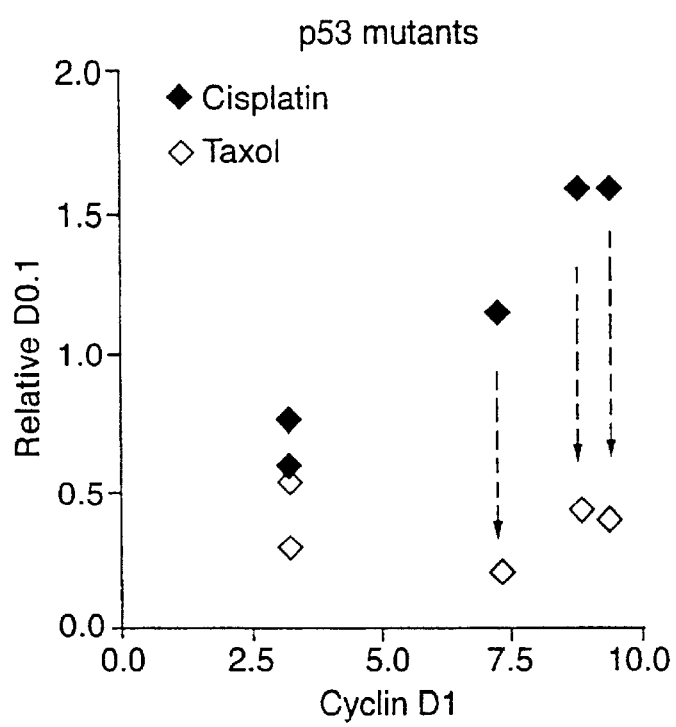
Figure 11:
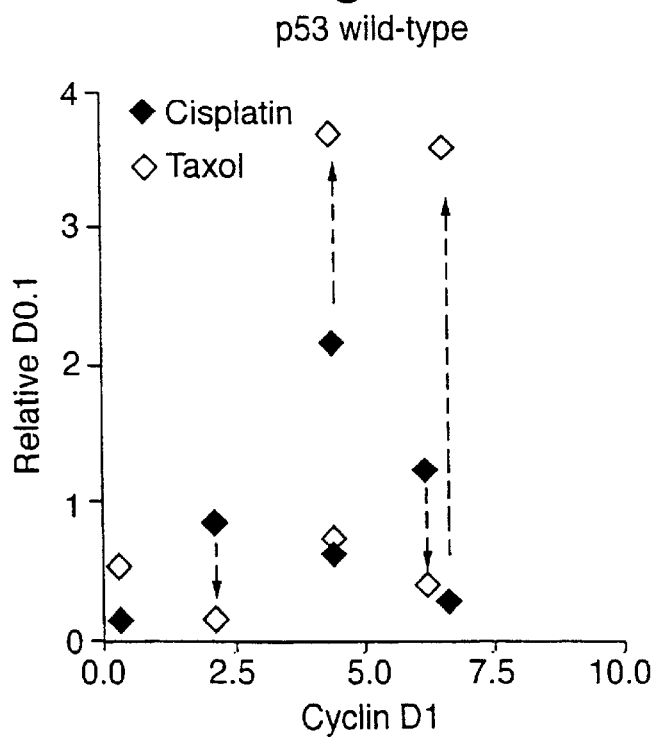

FIG. 3 shows a Western blot demonstrating the range of Raf-1 protein levels per total cellular protein, in particular the relative abundance of the 74 kD and 48 kD proteins, in the following 17 human in vitro cell lines:
  1. KB, oral epidermoid carcinoma
  2. HT29, adenocarcinoma, colon
  2. MGH-U1, bladder carcinoma
  4. HRT18, adenocarcinoma, rectum
  5. A431, squamous carcinoma vulva
  6. NCTC 2544, skin fibroblasts
  7. COR L23, large cell lung carcinoma
  8. SK-MEL3, melanoma
  9. AT5BIVA, ataxia telangiectasia fibroblast
  10. OAW42, ovarian carcinoma
  11. I407, embryonic intestinal epithelium
  12. 2780, ovarian carcinoma
  13. HEP-2, squamous carcinoma
  14. HX142, neuroblastoma
  15. RT112, bladder carcinoma
  16. HeLa, squamous carcinoma
  17. NCTC 2544 for a sample protein loading of 100 $\mu$g/50 $\mu$l on a 7.5% gel, the primary antisera being URP-2653 monoclonal against Raf-1 at a dilution of 1/750;

FIG. 4 shows the relationship between radiosensitivity measured as SF2 (log surviving fraction at 2 Gy) and Raf-1 abundance in wild-type p53 cell lines;

FIG. 5 shows the relationship between radiosensitivity measured as SF2 and Raf-1 abundance in mutant p53 cell lines;

FIG. 6 shows the relationship between radiosensitivity measured as SF2 and Raf-1 abundance in cell lines in which p21 protein levels are not elevated (undetectable);

FIG. 7 shows the relationship between radiosensitivity measured as SF2 and Raf-1 abundance in cell lines in which p21 protein levels are elevated;

FIG. 8 shows the relationship between the level of cyclin D1 protein and relative resistance to CDDP in cell lines in which p21 protein levels are not elevated (undetectable);

FIG. 9 shows the relationship between the level of cyclin D1 protein and relative resistance to CDDP in cell lines in which p21 protein levels are elevated;

FIG. 10 shows the relationship between the resistance to CDDP (CISPLATIN) (black points) and resistance to Paclitaxel (TAXOL) (white points) in mutant p53 cell lines, as the cyclin D1 levels increase;

FIG. 11 shows the corresponding relationship in wild-type p53 cell lines;

FIG. 12 shows the relationship between the resistance to CDDP (CISPLATIN) (black points) and the resistance to Paclitaxel (TAXOL) (white points) in cell lines in which p21 (p21 WAF1/CIP1) protein levels were substantially undetectable; and FIG. 13 shows the corresponding relationship in cell lines in which p21 WAF1/CIP1 protein levels were detectable.

In a first aspect, this invention relates to a method for predicting whether human cancer cells are likely to be sensitive to the cytotoxic effects of chemotherapeutic agents, such as platinating agents e.g. CDDP, by contemporaneously measuring the properties of two or more cancer-related genes. Moreover, the co-relationship between certain independently expressed cancer genes identified in this invention also provide previously undescribed targets against which to potentially direct therapy that is more cancer specific.

In particular, this embodiment relates to a method for measuring the resistance of p53 mutant cancer cells to the cytotoxic effects of a chemotherapeutic agent, which method comprises testing a sample comprising p53 mutant cells or an extract therefrom for the level of expression of Cyclin D1 or for the abundance of Cyclin D1 protein. This embodiment also relates to a kit for measuring the resistance of p53 mutant cancer cells to the cytotoxic effects of a chemotherapeutic agent, which kit comprises:
  (i) a means for testing for the level of expression of Cyclin D1 or for the abundance of Cyclin D1 protein; and (ii) a means for identifying p53 mutant cells.

In a similar embodiment, this invention relates to a method for measuring the resistance of cells to the cytotoxic effects of a chemotherapeutic agent, which method comprises testing a sample comprising cells or an extract therefrom for:

(a) the level of expression of p21, or for the abundance of p21 protein; and (b) the level of expression of Cyclin D1, or for the abundance of Cyclin D1 protein.

This embodiment also relates to a kit for measuring the resistance of cells to the cytotoxic effects of a chemotherapeutic agent, which kit comprises:

(i) a means for testing for the level of expression of p21, or for the abundance of p21 protein; and (ii) a means for testing for the level of expression of Cyclin D1, or for the abundance of Cyclin D1 protein.

Thus, this aspect preferably deals with measuring the levels of Cyclin D1 protein or Cyclin D1 expression, in cells whose p53 mutational status has been determined (e.g. by DNA sequencing) and/or cells displaying substantially undetectable p21 protein levels to determine the resistance of a tumour to, for example, CDDP. High cyclin D1 levels or high cyclin D1 expression, together with p53 mutation or non-elevated (preferably substantially undetectable) p21 protein levels (or substantial non-elevation (preferably substantial lack) of p21 expression), is strongly associated with resistance to chemotherapeutic agents such as CDDP in human cancer cells.

The over-expression of Cyclin D1, or the elevation of Cyclin D1 protein levels can be measured by any appropriate method, e.g. Western blotting. The point at which t is considered that the level is elevated or that the expression is over-expression is clear to the skilled person in this field, according to general teaching from the literature regarding usual levels of Cyclin D1 in human cell lines (see Oncogene, 1993, vol. 8, 2127–2133; and Oncogene, 1995, vol. 10, 775–778). This point can be determined according to the judgement of the individual carrying out the present method, depending on the particular cancer cells and patient involved.

Similarly, the expression of p21, or the level of p21 protein can be measured by any appropriate method, including methods corresponding to those referred to above for measuring Cyclin D1 levels. Specifically, p21 is a cyclin dependent kinase inhibitor which can be detected by Western blotting, immunocytochemistry or newer developing techniques, such as determining the relative abundance of p21 mRNA. The point at which it is considered that the p21 is effectively not expressed (or the expression is not elevated) or the p21 protein is effectively not detectable (or is effectively not elevated) is clear to the skilled person in this field, according to general teaching from the literature regarding usual levels of p21 protein in human cell lines (see Oncogene, 1995, vol. 11, 2021–2028; and Oncogene, 1996, vol.12(6), 1319–1324).

Human cancer cell lines with a combination of p53 mutation or substantially non-elevated (preferably substantially undetectable) p21 protein levels, and high levels of expression of the cyclin D1 protein are resistant to the cytotoxic effects of chemotherapeutic agents such as CDDP. This finding carries important clinical possibilities with regard to providing a potentially new parameter for predictive assays for CDDP responsiveness or a new target for modulating CDDP responsiveness.

The high correlation of p53 mutations and p21 protein levels, with high cyclin D1 levels or cyclin D1 over-expression also provides a potential target for drug development. Efforts are being made to develop drugs against mutant forms of p53 and independently, against cyclin D1. Such drugs are likely to be more effective when used together to treat cancers with the above p53 mutations and cyclin D1 over-expression. Such drugs might also be used in combination with other agents such as CDDP as potentiators of its effectiveness.

Figure 1:
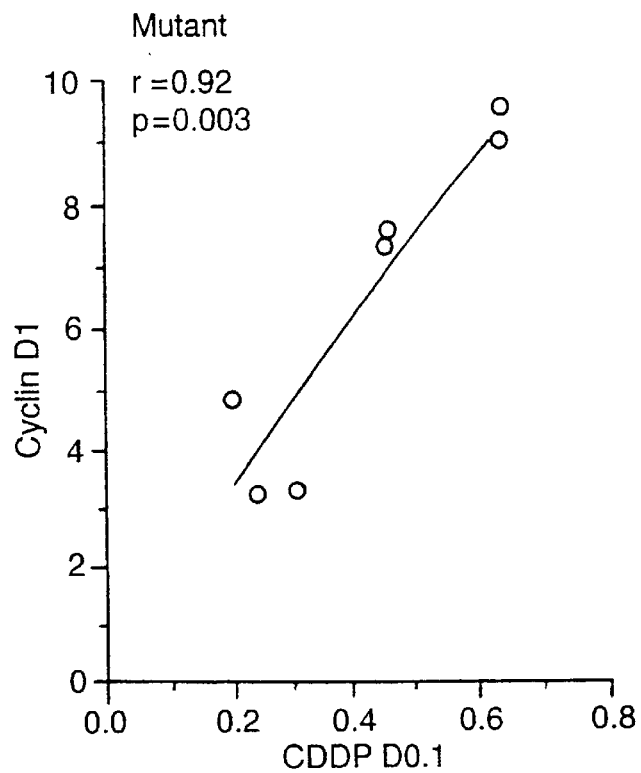
FIG. 1 shows the relationship between the level of cyclin D1 protein and relative resistance to CDDP in mutant p53 cell lines.

FIG. 1 shows that in p53 mutant human cell lines there is a strong relationship between the level of cyclin D1 protein and relative resistance to CDDP as measured by the D0.1 values. The implication is that human cancer cells with p53 mutations and high levels of cyclin D1 protein are unlikely to respond to platinating agents, such as CDDP, and alternative chemotherapeutic agents should be considered. The cyclin D1/p53 mutation test may also detect resistance to other cytotoxic drugs such as etoposide. Thus the test will indicate situations where radiation might be a viable alternative to CDDP, or whether other cytotoxic agents might be more appropriate.

Thus, as can be seen from the above, a clinical test may be developed for CDDP sensitivity based on the dual measurement of Cyclin D1 protein expression and the presence of mutations in the p53 gene. Cyclin D1 protein is typically measured by Western blotting or immunocytochemistry.

The determination of the mutational status of p53 can be effected by sequencing the genomic locus bearing the gene from the patient or by sequencing the expressed mRNA after conversion to cDNA. Various nucleic acid sequencing methodologies are available at present, all of which are appropriate for use with this diagnostic assay. The typical method would be based on incorporation of terminating nucleotides into polymerase generated copies of a template, using the method of Sanger et al, 1977. Many alternatives have arisen recently including adaptor sequencing (WO96/12039), ligation based sequencing (WO96/33205), sequencing by hybridisation (A. D. Mirzabekov, TIBTech 12:27–32, 1994) to list a few. Various methods for testing for specific mutations are known in the art, such as the TaqMan assay, oligonucleotide ligase assays, single strand conformational polymorphisms and assays based on hybridisation of template nucleic acids to oligonucleotide arrays.

Because cyclin D1 is a relatively short lived protein under cyclical transcriptional control, it is likely that mRNA levels for cyclin D1 will follow the same pattern as the cyclin D1 protein and show a similar strong relationship to CDDP resistance. This would make it possible to carry out a functional assay for resistance to CDDP by extracting mRNA from tumour samples and using this to determine the relative abundance of cyclin D1 mRNA and to detect mutations in the p53 mRNA.

Oligonucleotide Arrays

Determination of mRNA levels can be effected in a number of ways. One can readily convert poly-A bearing mRNA to cDNA using reverse transcription - a method is described in the example illustrating this invention. Reverse Transcriptase PCR (RTPCR) methods allow the quantity of single RNAs to be determined, but with a relatively low level of accuracy. Arrays of oligonucleotides are a relatively novel approach to nucleic acid analysis, allowing mutation analysis, sequencing by hybridisation and mRNA expression analysis. Methods of construction of such arrays have been developed, (see for example: A. C. Pease et al. Proc. Natl. Acad. Sci. USA. 91, 5022–5026, 1994; U. Maskos and E. M. Southern, Nucleic Acids Research 21, 2269–2270, 1993; E. M. Southern et al, Nucleic Acids Research 22, 1368–1373, 1994) and further methods are envisaged. Arrays that measure expression levels of mRNAs and detect mutations in those RNAs are being developed and these offer an attractive embodiment of the diagnostic test proposed by this invention.

Immunocytochemistry

An alternative embodiment of this invention can measure Cyclin D1 protein levels by immunocytochemistry using confocal laser fluorescence microscopy. Preferably a scanning system is used such as those described in WO92/10587, WO96/33508 and WO95/22058. Additionally, it is desirable that the microscopy system is also able to analyse multiple fluorescent dyes. In a preferred embodiment, antibodies against mutant forms of p53 are labelled with one dye, an antibody against cyclin D1 (sc-6281, Santa Cruz Biotechnology, CA) is labelled with a second dye whilst a third DNA binding dye can be used to select for aneuploid cells. DNA binding dyes such as HOECHST 33258 dye (bisbenzimide 2'-(4-hydroxyphenyl)-5-(4-methyl-1-piperazinyl)-2,5'-bi-1H-benzimidazole trihydrochloride pentahydrate), which binds AT-rich DNA or CHROMOMYCIN $A_3$ ($3^B$-O-(4-O-acetyl-2,6dideoxy-3-C-methyl-α-L-arabino-hexapyranoysyl)-7-methylolivomycin D), which binds GC-rich DNA, are appropriate. Antibodies exist against a number of known mutant forms of the p53 protein. A diagnostic test may comprise the steps of:

Extracting a biopsy of the tumour from a patient.

Optionally micro-dissecting that material to separate normal tissue from tumour material.

Preparing the biopsy material for microscopy which includes the steps of:

Labelling the biopsy material with the above fluorescently labelled antibody probes against Cyclin D1. The biopsy material may also, optionally be labelled with antibody probes against p53 mutant proteins and with a DNA binding dye.

Separating the labelled cells from unbound labelled probes.

Placing the labelled biopsy material in a scanning confocal microscope to count cells that:

Over-express or show elevated levels of cyclin D1, i.e. are labelled with at least a threshold quantity of antibody against cyclin D1.

Optionally, express mutant forms of p53, i.e. are labelled with at least the threshold quantity of antibodies against p53 mutants. Alternatively, p53 mutational status might be determined by analysis of the mRNA or genomic DNA as discussed above.

Optionally, have chromosomal amplifications as detected by the intensity of fluorescence from DNA binding fluorescent dyes.

Fluorescence Activated Cell Sorting

A further embodiment of the diagnostic test can exploit Fluorescence Activated Cell Sorting (FACS). A FACS instrument separates cells in a suspension in a manner dependent on the cells being labelled with a fluorescent marker. A typical FACS device operates as follows. Cells in a suspension travelling in single file are passed through a vibrating nozzle which causes the formation of droplets containing a single cell or none at all. The droplets pass through a laser beam. Fluorescence excited from each individual cell in its droplet by the laser is measured. After the detector the stream of cells in suspension pass through an electrostatic collar which gives the droplets a surface charge. The cells carrying droplets are given a positive or negative charge. If the drop contains a cell that fluoresces with an intensity above a particular threshold, the drop gets a charge of one polarity. Unlabelled cells get a charge of the opposite polarity. The charged droplets are then deflected by an electric field and depending on their surface charge are directed into separate containers and are counted Droplets that contain more than one cell scatter light more than individual cells which is readily detected and so these are left uncharged and enter a third disposal container. Multi-channel fluorescent detection devices have been constructed that can separate cells on the basis of labelling with multiple different fluorescent labels. These have multiple lasers which can excite fluorescence at different frequencies and the detector will detect different emission frequencies. A three label system is appropriate for this test. The same labelled probes as those described above for use in a confocal scanning fluorescence microscope would be appropriate. A diagnostic test might comprise the steps of:

Extracting a biopsy of the tumour from a patient.

Optionally micro-dissecting that material to separate normal tissue from tumour material.

Disrupting intracellular adhesion to form a single cell suspension.

Labelling the suspended cells with the above fluorescently labelled probes against cyclin D1. The biopsy material may also, optionally be labelled with antibody probes against p53 mutant proteins and with a DNA binding dye.

Separating the labelled cells from unbound labelled probes.

Passing the labelled cell suspension through a FACS device to count cells that:

Over-express or show elevated levels of cyclin D1, i.e. are labelled with the anti-cyclin D1 antibody above a threshold for 'normal' expression.

Optionally, express a mutant form of p53, i.e. are labelled with at least a threshold quantity of antibody against mutant forms of p53.

Optionally, have chromosomal amplifications as detected by the intensity of fluorescence from DNA binding fluorescent dyes.

Modulation of Cyclin D1 Expression in p53 Mutant Human Cancers

At present many attempts are being made to develop drugs which inhibit cyclin D1. As this molecule has a vital function in controlling the progress of normal cells through the 'start' component of the G1/S checkpoint such inhibitors would be likely to be extremely non-selective and very toxic to normal cells. The more specific relationship of resistance to CDDP and sensitivity to taxanes in p53 mutant human cancer cells having elevated cyclin D1 levels described here provides a much more defined target for novel therapeutic agents which could potentially used in conjunction with taxanes, this being an agent with a proven track record of curing many (though by no means all) cancers. This approach is based on a concept of starting with therapeutic agents which already work to some extent and using techniques such as gene targeting to enhance the efficacy of already available therapeutic agents.

In the case of patients who have mutant forms of p53, it may be possible to increase their responsiveness to platinating agents by decreasing their levels of cyclin D1. Cyclin D1 inhibitors are likely to be non-selectively toxic, but if administered at low doses in conjunction with an agent such as a taxane, the combination may be more effective against tumours than either alone, particularly to cells over-expressing cyclin D1.

In a second aspect, this invention relates to a method for predicting whether human cancer cells are likely to be radiosensitive, by contemporaneously measuring the properties of two or more cancer-related genes.

This aspect of the invention preferably relates to an assay which can be used as a clinical assay to predict whether cancer cells are likely to respond to radiotherapy. This aspect of the invention makes use of an antibody against Raf-1 which is specific for that protein, to facilitate cheaper diagnostic tests. This aspect further concerns a method, using the antibody, for predicting whether cancer cells are likely to respond to radiotherapy by contemporaneously measuring the properties of two or more cancer-related genes.

Specifically, this embodiment concerns a method for measuring the radiosensitivity of wild-type p53 cancer cells, which method comprises testing a sample comprising wild-type p53 cells or an extract therefrom, for the level of expression of Raf-1 or for the abundance of Raf-1 protein, wherein when the testing is carried out using Western blotting, an antibody specific to Raf-1 is employed. This embodiment also relates to a kit for measuring the radiosensitivity of wild-type p53 cancer cells, which kit comprises:

(i) a means for testing for the level of expression of Raf-1, or for the abundance of Raf-1 protein; and (ii) a means for identifying wild-type p53 cells.

A similar embodiment of the present invention concerns a method for measuring the radiosensitivity of cells, which method comprises testing a sample comprising cells or an extract therefrom for:

(a) the level of expression of p21, or for the abundance of p21 protein; and (b) the level of expression of Raf-1, or for the abundance of Raf-1 protein.

The order in which steps (a) and (b) is carried out is not particularly limited. Thus, step (a) may precede step (b), or alternatively step (b) may precede step (a). This embodiment also concerns a kit for measuring the radiosensitivity of cells, which kit comprises:

(i) a means for testing for the level of expression of Raf-1 or for the abundance of Raf-1 protein; and (ii) a means for testing for the level of expression of p21 or for the abundance of p21 protein.

Accordingly, the second aspect preferably concerns a method for measuring the radiosensitivity of wild-type p53 cancer cells or cells in which p21 protein levels are detectable preferably elevated), which method comprises testing a sample comprising wild-type p53 cells or an extract therefrom, or cells in which p21 protein levels are detectable (preferably elevated) or an extract therefrom, for the abundance of Raf-1 protein, wherein the testing is carried out using an antibody specific to Raf-1 protein.

Determination and interpretation of p21 levels has already been discussed above. The level of expression of Raf-1, or the elevation of Raf-1 protein levels can be measured by any appropriate method, as discussed above, e.g. Western blotting. The point at which it is considered that the protein level, or the expression, is elevated to a sufficient degree above normal indicating useful radiosensitivity, is clear to the skilled person in this field, according to general teaching from the literature regarding usual levels of Raf-1 in human cell lines (see European Journal of Cancer, B Oral Oncology, 1995, November, 31B(6), 384–391). This point can be determined according to the judgement of the individual carrying out the present method, depending on the particular cancer cells and patient involved.

This aspect of the present invention makes use of a method for producing an antibody specific to Raf-1 protein, which antibody does not cross-react with a 48 kD protein co-present in cells containing Raf-1 protein, which method comprises forming a peptide which comprises or forms part of an epitope on the Raf-1 protein that is not present on the 48 kD protein, and preparing an antibody against the peptide. This aspect of the invention also makes use of a further method for producing an antibody specific to Raf-1 protein, which antibody does not cross-react with a 48 kD protein co-present in cells containing Raf-1 protein, which further method comprises immunising an animal with Raf-1 protein and an antibody specific to the 48 kD protein so as to mask potential epitopic sites on Raf-1 protein which are also present on the 48 kD protein, and obtaining an antibody against the masked Raf-1 protein.

This aspect specifically deals with measuring the levels of the Raf-1 protein product of the C-Raf-1 proto-oncogene, in cells whose p53 mutational status or p21 levels have been identified, preferably in the case of p53 by DNA sequencing, to determine the radiosensitivity of the tumour and consequently whether radiotherapy is an appropriate treatment for the patient. In a background of unmutated p53 or elevated p21 protein, the higher the level of Raf-1 expression the greater the sensitivity of the tumour to ionising radiation.

Whilst the mechanisms explaining the observed relationships between radiosensitivity, cell cycle progress and the functions of Raf-1, p53 and p21 remain obscure, the strong relationship between Raf-1 and radiosensitivity in human cancer cells expressing wild-tape p53 or detectable (preferably elevated) p21 levels, permits the development of a dual parameter Raf-1/p53 or Raf-1/p21 test for clinical radiosensitivity.

FIG. 4 shows that in p53 wild-type cell lines, the higher the Raf-1 protein, the more radiosensitive the cells are as measured by log surviving fraction at 2 Gy (SF2). On the other hand, FIG. 5 shows that in the presence of p53 mutations there is little or no relationship between Raf-1 levels and radiosensitivity. FIG. 6 shows that in cell lines in which p21 protein levels are not elevated there is little or no relationship between Raf-1 levels and radiosensitivity, whereas FIG. 7 shows that in cell lines in which p21 protein levels are elevated the higher the Raf-1 protein, the more radiosensitive the cells are as measured by log surviving fraction at 2 Gy (SF2).

The clinical test requires determination of the mutational status of p53 as wild-type, in conjunction with measuring the level of Raf-1 expression in biopsy material from tumours in patients. Alternatively the test requires determination of the level of p21 protein, in conjunction with measuring the level of Raf-1 expression of biopsy material from tumours in patients. The levels of p21 protein can be determined as discussed above. The determination of the mutational status of p53 can be effected by sequencing the genomic locus bearing the gene from the patient or by sequencing the expressed mRNA after conversion of cDNA. Various nucleic acid sequencing methodologies are available at present, all of which are appropriate for use with this diagnostic assay. The typical method would be based on incorporation of terminating nucleotides into polymerase generated copies of a template, using the method of Sanger et al., 1977. Any alternatives have arisen recently including adaptor sequencing (WO96/12039), ligation based sequencing (WO96/33205) and sequencing by hybridisation to oligonucleotide arrays (A. D. Mirzabekov, TIBTech 12:27–32, 1994) to list a few. Various methods for testing for specific mutations exists such as the TaqMan assay or oligonucleotide ligase assays. However, these may not be entirely appropriate since the absence of known mutations may not necessarily imply that p53 in a tumour is in fact wild-type.

Determination of the expression level of Raf-1 is effected by measuring the abundance of the Raf-1 protein. Raf-1 protein levels can be measured by immunocytochemistry or flow cytometry (FCM). Previously there was a problem with the latter approach arising out of cross-reactivity of existing antibodies with non-Raf-1 proteins. Until the present, there were no available antibodies to Raf-which did not also cross-react with a very abundant but irrelevant 48 kD protein on Western blotting. Techniques such as immunocytochemistry or FCM would only give non-specific results. This necessitated some form of molecular separation, such as by electrophoresis in Western blotting, to separate Raf-1 (a 72–74 kD protein) from the irrelevant 48 kD species. Column chromatography techniques were appropriate, such as gel filtration or ion exchange chromatography. High Performance Liquid Chromatography or Capillary Electrophoresis were also usable as separation techniques. These could all be followed by an immunoassay. Other means of specific recognition may also have been conceivable, including the development of RNA aptamers to the Raf-1 protein. However, all of these techniques are time consuming and expensive, making them inappropriate for a clinical test. The availability of an antibody specific to Raf-1 allows diagnostic assays to be carried out without the need for separation.

The first method for producing the antibody used in the present invention required isolation and identification of the 48 kD cross-reacting epitope, so that its DNA and protein genetic sequence could be determined. This information was used to compare the 48 kD protein sequence with the full length Raf proto oncogene protein sequence to choose an epitope on the full length proto-oncogene protein that is not shared by the 48 kD protein. This could be achieved using a cell line with high Raf-1 and 48 kD protein levels, such as NCTC 2544 (see FIG. 3). Quantities of lysate were produced and the 48 kD protein purified. Purification could be achieved using immunoprecipitation or affinity purification with a monoclonal antibody produced by the inventors, or with a commercial anti-Raf-1 antibody, both of which have been shown on Western blotting to bind strongly to both the 72–74 kD and the 48 kD protein. The cells producing the monoclonal antibody were grown up in high yields for affinity chromatography as ascites in Balb/C mice. The antibody from the ascitic fluid was reacted with cyanogen bromide sephacryl and the antibody-sephacryl used to make an affinity column. The lysates from the NTCT cells were loaded onto the affinity column, non-specific material was washed through and 48 kD and 72–74 kD molecules sharing the same epitope and bound to the antibody on the column were eluted at low pH. The immunoprecipitate or eluate from the affinity chromatography column was then concentrated, a protein estimation carried out and 150 µg per well was run on 10–20 adjacent wells in 10% SDS polyacrylamide gel electrophoresis with molecular markers. The 48 kD band was then excised and as long, an amino acid sequence as possible was sequenced from the N-terminus (or alternatively from the C-terminus). Using the peptide sequence primers were prepared whose genetic sequences match the protein sequences (allowing for the degeneracy in the coding for certain amino acids) for the N- (or C-) terminus. A series of PCRs was run until a 48 kD length of DNA was obtained. This was then sequenced. A sequence comparison between the 48 kD and the 72–74 kD full length Raf-1 proto-oncogene enabled the rational design of synthetic peptides from potential epitopes on the full length 72–74 kD Raf proto-oncogene protein, which were not present on the 48 kD protein. The unique synthetic peptides were used to prepare polyclonal and monoclonal antibodies which reacted against the Raf-1 protein, but not the 48 kD protein, these antibodies being valuable in flow or confocal microscopic cytometry and/or immunofluorescence or immunocytochemistry.

The second method for producing the antibody used in the present invention required immunisation of an animal with Raf protein in addition to an antibody against the 48 kD protein. For example, either the 72–74 kD full length Raf-1 protein (produced from the DNA sequence in an expression vector in bacteria) can be pre-incubated with previously available anti Raf-1 antibodies (which cross-react with the 48 kD protein) and the resulting immune complexes separated by centrifugation and then injected into an animal (such as a mouse), or the anti Raf-1 (anti 48 kD protein) antibodies and the full length 72–74 kD Raf-1 protein can be injected separately into the same animal. Polyclonal and monoclonal antibodies were prepared using the full length 72–74 kD Raf proto-oncogene protein as immunogen. The protein was produced by the recombinant Raf-1 gene in an expression vector. The antibody against the 48 kD protein was a commercially available antibody. Its function was to cover potential epitopic sites on the Raf protein which cross-react with the 48 kD protein. Such a masked Raf protein immunogen more selectively stimulates the production of antibodies which recognise the full length 72–74 kD Raf proto-oncogene protein rather than the 48 kD protein.

Thus, using the above antibody to measure Raf-1 protein levels, a reliable clinical assay is provided for the determination of the radiosensitivity of human cancer cells.

In a third aspect, this invention relates to a method for selecting a chemotherapeutic agent for treating cancer, by contemporaneously measuring the properties of two or more cancer-related genes.

In particular, this embodiment relates to a method for selecting a chemotherapeutic agent for treating cancer, which method comprises:

(a) testing a sample comprising p53 mutant cells, or an extract therefrom for the level of expression of Cyclin D1 or for the abundance of Cyclin D1 protein, and (b) if Cyclin D1 is over-expressed, and/or Cyclin D1 protein is present at elevated levels, selecting for treatment a chemotherapeutic agent comprising a taxane;

(c) if Cyclin D1 is not overexpressed and/or Cyclin D1 protein is substantially not present at elevated levels, selecting for treatment a chemotherapeutic agent comprising an agent other than a taxane.

This embodiment also relates to a kit for selecting a chemotherapeutic agent for treatment, which kit comprises:

(a) a means for identifying p53 mutant cells; and (b) a means for testing for the level of expression of Cyclin D1 or for the abundance of Cyclin D1 protein in cells or in a sample therefrom.

In a similar embodiment, the present invention concerns a method for selecting a chemotherapeutic agent for treating cancer, which method comprises:

(a) testing a sample comprising cells that substantially do not express p21 and/or in which p21 protein is substantially undetectable, or an extract therefrom for the level of expression of Cyclin D1 or for the abundance of cyclin D1 protein; and (b) if cyclin D1 is overexpressed, and/or cyclin D1 protein is present at elevated levels, selecting for treatment a chemotherapeutic agent comprising a taxane;

(c) if cyclin D1 is not overexpressed and/or cyclin D1 protein is substantially not present at elevated levels, selecting for treatment a chemotherapeutic agent comprising an agent other than a taxane.

This embodiment also provides a kit for selecting a chemotherapeutic agent for treatment, which kit comprises:
(a) a means for identifying cells in which p21 is substantially not expressed and/or p21 protein is substantially undetectable; and
(b) a means for testing for the level of expression of Cyclin D1 or for the abundance of cyclin D1 protein in cells or in a sample therefrom.

Thus, this third aspect preferably deals with a method for selecting a chemotherapeutic agent for treating cancer, which method comprises:
(a) testing a sample comprising:
   (i) p53 mutant cells, or an extract therefrom,
   (ii) or cells that substantially do not express p21 and/or in which p21 protein is substantially undetectable, or an extract therefrom for the abundance of cyclin D1 protein, and
(b) if cyclin D1 is over-expressed, and/or cyclin D1 protein is present at elevated levels, selecting for treatment a chemotherapeutic agent comprising a taxane;
(c) if cyclin D1 is not over-expressed and/or cyclin D1 protein is substantially not present at elevated levels, selecting for treatment a chemotherapeutic agent comprising an agent other than a taxane.

The level of cyclin D1 protein or cyclin D1 expression can be measured as described above. Similarly, the level of p21 expression or p21 protein can be measured as described above. The meaning of over-expression of cyclin D1 and the meaning of undetectable p21 are also discussed above.

Human cancer cell lines with a combination of p53 mutation and high levels of expression of the cyclin D1 protein are resistant to the cytotoxic effects of chemotherapeutic agents such as CDDP, but are sensitive to taxanes. Similarly, human cancer cell lines with a combination of substantially undetectable p21 protein levels and high levels of expression of the cyclin D1 protein are also resistant to the cytotoxic effects of chemotherapeutic agents such as CDDP, but are sensitive to taxanes. These findings carry important clinical possibilities with regard to providing a potentially new parameter for predictive assays for taxane responsiveness or a new target for modulating taxane responsiveness.

The high correlation of taxane sensitivity to CDDP resistance in cells with p53 mutations or substantially absent p21 protein, and high cyclin D1 levels or cyclin D1 overexpression also provides a potential target for drug development, As mentioned above, efforts are being made to develop drugs against mutant forms of p53 and independently, against cyclin D1. Such drugs are likely to be more effective when used together to treat cancers with the above p53 mutations and cyclin D1 overexpression. Such drugs might also be used in combination with other agents such as Paclitaxel (TAXOL) as potentiators of its effectiveness.

FIG. 10 shows that in p53 mutant human cell lines with high cyclin D1 levels or cyclin D1 overexpression there is a strong relationship between resistance to CDDP and sensitivity to Paclitaxel TAXOL), as measured by the D0.1 values (the dose of the drug which reduces clonogenic survival to 10% of the control, untreated cells). Thus human cancer cells with p53 mutations and high levels of cyclin D1 protein which do not respond to CDDP will very likely respond to taxanes as an alternative therapy. The cyclin D1/p53 mutation test may also indicate a correlation of taxane sensitivity to resistance to other cytotoxic drugs such as etoposide.

A clinical test may be developed for taxane sensitivity based on the measurement of Cyclin D1 protein expression and the presence of mutations in the p53 gene. Cyclin D1 protein is typically measured by Western blotting or immunocytochemistry.

A specific example of a chemotherapeutic agent, the resistance against which is often compared with taxane sensitivity, is CDDP. Thus using the present invention, in appropriate cases CDDP can be ruled out of the treatment regime before treatment beings and replaced with Paclitaxel (TAXOL). Further examples of agents which can be replaced with taxanes include other platinating agents, such as carboplatin and paraplatin as well as other chemotherapeutic agents, for example alkylating agents, DNA intercalating agents such as Doxorubicin, topoisomerase inhibitors, anti-metabolites such as methotrexate, 5-fluorouracil, DNA synthesis inhibitors such as cytosine arabinoside, and mitotic inhibitors such as the vinca alkaloids.

EXAMPLE 1

Sensitivity to CDDP Using p53/ Cyclin D1 Relationship

Human in vitro cell lines of different histological origin which exhibit a range of intrinsic sensitivity to cytotoxic drugs as measured by clonogenic cell survival assays, have been shown to provide appropriate models of the response of clinical tumours to chemotherapy. In particular, these cell lines exhibit the range of sensitivities to cytotoxic drugs and ionising radiation usually encountered in the clinic. These human in vitro cancer cell lines are now widely recognised as relevant models for the clinical response of tumours to chemotherapy. Intrinsic sensitivity to cytotoxic agents is measured by clonogenic assays of a range of human cancer cell lines. It is therefore possible to identify genes whose expression and/or mutational status is related to intrinsic sensitivity to cytotoxic agents in a wide range of human in vitro cell lines by measuring the expression of target genes and/or determining their mutational status and correlating these parameters to cell line sensitivity to cytotoxic agents. This procedure has identified genes relevant to clinical responsiveness to CDDP. Discoveries in human in vitro cell lines, such as those leading to this invention, therefore, have a strong possibility of being able to be translated into clinically useful tests for how well cancers may be expected to respond to treatment. The body of work that has been carried out to measure the clonogenic cell survival of a wide range of human in vitro cell lines of different histology after exposure to CDDP is described below.

Materials and Methods

Cell lines and Clonogenic Cell Survival Assays

The growth characteristics clonogenic assay procedures of the human in vitro cell lines used in this analysis have already been reported (Warenius et al 1994). The cell lines are listed, with their histological classification in Table 1. All are well established; many having been growing in vitro for several years. Cell lines were either donations or purchased by our laboratories. On receipt all were grown for 5 passages to provide sufficient cells for batch storage in liquid nitrogen. During this period contamination was excluded by at least one passage in antibiotic free medium and mycoplasma testing was carried out on all lines. For clonogenic assays, cells were taken from a designated primary liquid nitrogen batch and grown for 3–6 passages until there were sufficient well-growing cells. Further batches from these cells were frozen in liquid nitrogen. Cells were routinely maintained in DMEM medium except RT112 and H322, which were grown in RPMI1640 and MGHU-1 which were grown in Ham's F12 medium. All lines were supplemented with 10% heat-inactivated foetal calf serum (HIFCS).

TABLE 1 p53 mutational status

| Cell Line | | cDNA sequence | Amino-acid change | p53 protein |
|---|---|---|---|---|
| I407 | Embryonic intest. epith. | Normal | none | Wild-type |
| HEP 2 | Squamous carcin. larynx | Normal | none | wild-type |
| MGHU 1 | Transit. carcinoma bladder | Normal | none | Wild-type |
| HRT 18 | Adenocarcinoma rectum | Normal | none | Wild-type |
| 2780 | Ovarian carcinoma | Normal | none | Wild-type |
| OAW 42 | Ovarian carcinoma | CGA-CGG codon 213 | none | Wild-type |
| HT 29/5 | Adenocarcinoma colon | CCT-CAT codon 273 | Arg-His | Mutant |
| COLO 320 | Adenocarcinoma colon | CGG-TGG codon 245 | Arg-Tryp | Mutant |
| H 322 | Small cell carcinoma lung | CGG-TGG codon 245 | Arg-Tryp | Mutant |
| H 417 | Small cell carcinoma lung | GAG-TAG codon 298 | Glu-Stop | Truncated |
| RPMI 7951 | Melanoma | TCA-TTA codon 166 | Ser-Stop | Truncated |
| RT 112 | Transit. carcinoma bladder | CCG-CAG codon 248 | Arg-Gly | Mutant |
| MOR | Adenocarcinoma lung | C deletion codon 152 | Frameshift 178 aa | Truncated |
| MEL 2 | Melanoma | CGC-AGC codon 245 | Gly-Ser | Mutant |

In order to assay CDDP sensitivity $10^2$–$10^5$ cells were plated in 3 ml of Ham's F12 medium supplemented with 10% FCS in 6 well plates and incubated at 3° C. in an atmosphere of 5% $CO_2$ for 8 hours. Dilutions of 0.02–2.0 μg/m from a 1 mg/ml stock solution of CDDP (light protected) were then made and 1 ml of the appropriate dilution were added to each plate to give a final volume of 4 ml. The plates were then incubated at 37° C. in an atmosphere of 5% $CO_2$ in darkness for 14 days in the presence of the CDDP. The medium was then removed, the cells were fixed in 70% ethanol and stained with 10% Giemsa and colonies of >100 cells counted. One 6 well plate was used for each drug dilution. The data points from all the assays were pooled. A minimum of 3 separate clonogenic assays with 6 points/drug dose/assay were necessary for each cell line. CDDP cell survival was determined at the 10% clonogenic cell survival level (D0.1) by interpolation of the fitted regression curve.

Identification of Mutations in the p53 Gene by PCR and DNA Sequencing

Material for PCR and DNA sequencing of p53 and Western blotting for cyclin-D1 protein, was obtained from the same liquid nitrogen batches used to provide cells for clonogenic cell survival data. Cells were grown for up to three passages prior to being subjected to the following procedures:

Nucleic Acid Isolation

RNA and genomic DNA were prepared from the cell lines described here by the guanidinium isothiocyanate CsCl gradient method (Chirgwin et al, 1979, Barraclough et al, 1981). Briefly, the cells were collected in ice-cold phosphate-buffered saline (PBS) and homogenised in guanidinium isothiocyanate buffer (4M guanidinium isothiocyanate, 50 mM Tris pH 7.5, 25 mM EDTA pH 8.0, 0.5% (w/v) sodium lauryl sarcosine and 8% (v/v) 2-mercaptoethanol added just prior to use. The homogenate was cleared by centrifugation at 8,000 rpm for 10 mins at 4° C. (SS34 rotor, Sorvall RC-5B centrifuge) and the RNA pelleted by centrifugation of the homogenate through a cushion of 5.7M caesium chloride/0.1M EDTA at 32,000 rpm for 20 hr at 20° C. (TST 41.14 rotor, Kontron Centrikon T20 60 ultracentrifuge). The pellet of RNA was redissolved in 0.1% (w/v) SDS and precipitated with ethanol overnight at −20° C. before quantitation.

Polymerase Chain Reaction, cDNA Synthesis and Nucleotide Sequencing

PCR (for exons 2–8 and for exons 9–11) was performed on DNA and RNA extracted from the human carcinoma cell lines. Each exon was then examined by DNA sequencing.

PCR Primers were designed flanking each exon and synthesised on an Applied Biosystems 381A DNA synthesiser. Each exon was amplified separately with the exceptions of exons 2 and 3 which were amplified as a unit, and exons 9, 10 and 11 which were amplified together by reverse transcription polymerase chain reaction (RTPCR). The following primers were used:

Exon 2/3 sense 5'-CCC ACT TTT CCT CTT GCA GC-3' (SEQ ID NO:1)

Exon 2/3 antisense 5'-AGC CCA ACC CTT GTC CTT AC-3' (SEQ ID NO:2)

Exon 4 sense 5'-CTG CTC TTT TCA CCC ATC TA-3' (SEQ ID NO:3)

Exon 4 antisense 5'-GCA TTG AAG TCT CAT GGA AG-3' (SEQ ID NO:4)

Exon 5 sense 5'-TGT TCA CTT GTG CCC TGA CT-3' (SEQ ID NO:5)

Exon 5 antisense 5'-CAG CCC TGT CGT CTC TCC AG-3' (SEQ ID NO:6)

Exon 6 sense 5'-GCC TCT GAT TCC TCA CTG AT-3' (SEQ ID NO:7)

Exon 6 antisense 5'-TTA ACC CCT CCT CCC AGA GA-3' (SEQ ID NO:8)

Exon 7 sense 5'-ACT GGC CTC ATC TTG GGC CT-3' (SEQ ID NO:9)

Exon 7 antisense 5'-TGT GCA GGG TGG CM GTG GC-3' (SEQ ID NO:10)

Exon 8 sense 5'-T ATC CTG AGT AGT GG-3' (SEQ ID NO:11)

Exon 8 antisense 5'-T GCT TGC TTA CCT CG-3' (SEQ ID NO:12)

Exon 9/10/11 sense 5'-AGA MG GGG AGC CTC ACC AC-3' (SEQ ID NO:13)

Exon 9/10/11 antisense 5'-CTG ACG CAC AGC TAT TGC AA-3' (SEQ ID NO:14)

Genomic DNA was digested with EcoR1 and precipitated with ethanol and resuspended in 50 μl of water (Sigma) before being subjected to PCR amplification. The DNA (1 μg) was amplified in 50 μl PCR reactions containing 20 pmoles of each primer. A 'hot start' PCR protocol was used with the dNTP's and Taq enzyme initially separated from the rest: of the reaction components on a wax cushion. The reactions were placed in a pre-heated PCR block at 95° C. for 2 minutes before undergoing thirty cycles of denaturation (30s at 95° C.), annealing (30s at 60° C. for exons 2–3, 4 and 6; 65° C. for exons 5 and 8; 67° C. for exon 7; and 68° C. for exon 9–11) and extension (1 min at 72° C.). The PCR products were checked on a 0.8% (w/v) agarose gel before being purified using a Wizard minicolumn (Promega), and used directly in sequencing reactions.

cDNA Synthesis and RTPCR

Complementary DNA was synthesised from approximately 5 μg of total RNA using oligo (dT) as a primer. Total RNA (5 μg), human placental ribonuclease inhibitor (HPRI) 20U and 1 μg oligo (dT) were heated at 70° C. for 10 minutes, chilled on ice, added to 1×first strand buffer (50 mM Tris-HCl, pH 8.3, 75 mM potassium chloride and 3 mM magnesium chloride), 0.01M DTT, dNTPs (0.5 mM for each deoxyribonucleoside triphosphate), 400U of Superscript Reverse Transcriptase (Gibco) and incubated at 37° C. for 1 hour. PCR for exons 9 to 11 was carried out using 5 μl of the above incubation in a $^{50}$ μl of PCR reaction as described in the previous section.

Nucleotide Sequencing

Sequencing primers (10 pmoles) were radioactively labelled at their 5' ends with $^{32}$P-ATP (45 μCi) at 37° C. for 30 min in a reaction containing T4 Polynucleotide Kinase (PNK) (9.7U, Pharmacia) and 1×T4 PNK buffer (10 mM Tris-acetate, 10 mM magnesium acetate and 50 mM potassium acetate). The primers used were identical to those employed in the PCR reactions except for exon 5 for which a separate sense sequencing primer was designed as follows; 5'-TAC TCC CCT GCC CTC-3' (SEQ ID NO:15). Sequencing was carried out by the dideoxynucleotide enzymatic method (Sanger et al, 1977), using the fmol DNA Sequencing System (Promega). Any putative sequence mutations identified were confirmed by additional sequencing of the exon in the antisense direction as well as by carrying out a repeat PCR and sequencing of the cell line.

Western Blotting for Cyclin D1

Two independent Western blottings with lysates for each cell line loaded in pairs on each gel were carried out. Standard conditions were used for the preparation of cells for lysates for Western blotting on each of the cell lines; $10^7$ cells were grown in 162 cm$^1$ tissue culture flasks (Costar Ltd., High Wycombe, Bucks) until they were pre-confluent but still growing exponentially as confirmed by flow cytometry. Cells were then removed by trypsinisation, resuspended in complete medium±10% FCS and washed 3 times by serial centrifugation and resuspension in PBS without serum. 1–3×10$^8$ viable cells were then pelleted by centrifugation and resuspended at 3×10$^7$ cells per ml of lysate buffer (Stock solution: 10% SDS 10 ml., 0.5M Tris pH 6.8, glycerol 10 ml., Double distilled water 62 ml. To 10 ml of stock solution were added 100 ml of 10 mM Leupeptin+10 ml 100 mM PMSF). Protein estimations were performed and the final concentration of the lysates adjusted to 300 μg total cellular protein per 100 μl. To measure cyclin D1 protein, 150 μg of total cellular protein in 50 μl of lysate buffer was added per lane well to a 7.5% Laemmli separating gel and electrophoresis carried out at 16° C. using 60 V over 16 hours and a constant current of 500 mA. Blots were transferred to nitrocellulose at 22° C. over 16 hours using to a semi-dry blotting apparatus (Biorad, Richmond, Calif.) incubated with the a mouse IgG$_1$ monoclonal antibody to mammalian cyclins (G124–259.5, Pharmingen) and then incubated with rabbit anti-mouse conjugated antibodies (Dako, UK) at ⅟1000 and developed in alkaline phosphatase buffer containing Nitroblue Tetrazolium and 5-Bromo-4-Chloro-3-Indoyl Phosphate, (Sigma, Poole, Dorset, UK) (50 mg/ml in dimethylformamide) for 1 hr at room temperature in darkness. Colour development was arrested with double distilled water, and the blots were dried flat. Cyclins were clearly resolved as distinct bands, cyclin D1 having the lowest mobility.

Quantitation of the protein product of the cyclin D1 gene was carried out by measurement of optical density on a Schimadzu scanning densitometer with tungsten light and expressed as O.D. units per 150 μg of total cellular protein. Titration curves obtained by loading different amounts of total cellular protein have previously shown that linear relationships for optical density (O.D.) could be obtained over the range found for cyclin D1 protein across the cell lines (Warenius et al 1994, Browning 1997). In order to compare different cyclin D1 protein levels between the cell lines, the mean O.D. value for all the lines was calculated and the relative O.D. for cyclin D1 protein in each individual cell line was normalised to the mean O.D. and multiplied by an arbitrary value of 5.0.

Results

Mutations were found in mRNA expressed from the p53 gene in a number of cell lines (see Table 1). The mutations identified in the cell lines described here were in exons 5–8 which are known to contain the majority of p53 mutations (Hollstein et al, 1991). All these mutations have been previously described apart from the nonsense mutation identified in codon 166 of the RPMI7951 line. This along with the G to T transversion in codon 298 of H417 did not lie within the most highly conserved region of the p53 gene. In the OAW42 ovarian carcinoma cell line the single base missense mutation from CGA to CGG was silent, so that the mutant triplet still coded for the same amino acid (Arg) as is present in wild-type p53 (wtp53) protein. A normal p53 protein was thus expressed in half of the cell lines. The mRNA of the other half of the cell lines coded for abnormal p53 protein. RPMI7951 and H417 possessed stop mutations resulting in 165 and 297 amino acid truncated proteins respectively. COLO320 and H322 independently exhibited a missense G:C to A:T mutation at the same site resulting in an amino-acid substitution from Arg to Tryp. RT112 and HT29/5 also had mutations coding for changes in Arg (to Gly and His respectvely). COLO320, H322 and RT112 were homozygous for p53 mutations. The other mutant lines showed evidence of retention of heterozygosity. HT29/5 and RPMI7951 both expressed small amounts of wild-type p53 mRNA though H417 expressed relatively high levels.

The relationship between cyclin D1 levels and CDDP sensitivity was examined for all cell lines and then independently in the wtp53 and mp53 cells. The ranges of cyclin-D1 protein levels in wtp53 cells and mp53 cells overlapped (3.33–10.39 and 3.58–8.46 respectively). Only in p53 mutant cells was a useful correlation found between cyclin D1 protein levels and resistance to CDDP.

Figure 2:
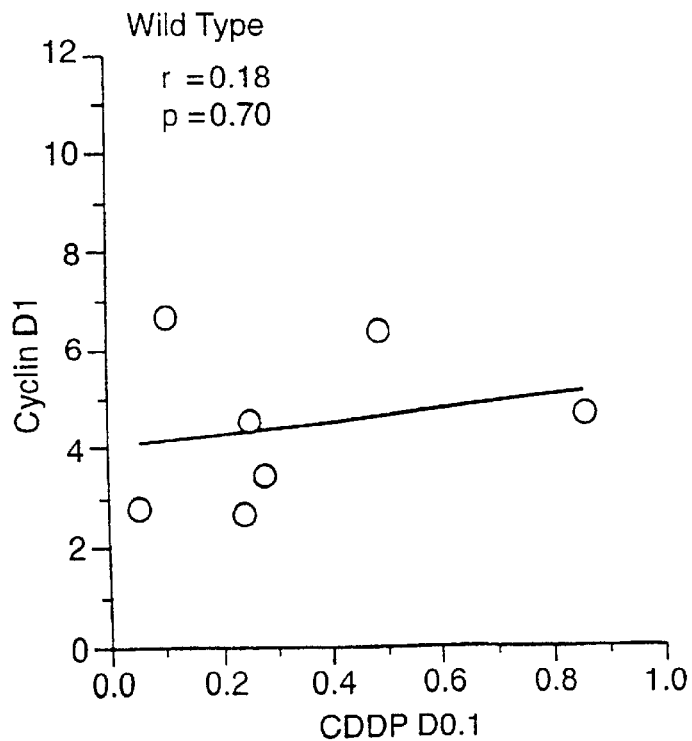
FIG. 2 shows the corresponding relationship in wild-type p53 cell lines.

Thus, in mutant p53 cell lines, the higher the cyclin D1 levels, the more likely it is that the cells are resistant to CDDP (FIG. 1). This correlation is not found in wild-type p53 cell lines (FIG. 2).

EXAMPLE 2

Sensitivity to CDDP Using p21/Cyclin D1 Relationship

A number of cell lines were selected and their resistance to CDDP was tested as in Example 1 in combination with their levels of cyclin D1 protein. The p21 protein levels of these cells was also measured using Western blotting according to substantially standard methods. The results for cell lines in which p21 protein levels were not elevated (undetectable) are shown in FIG. 8, whilst the results for cell lines in which p21 protein levels were elevated are shown in FIG. 9. In the case where p21 protein levels were not elevated, the higher the cyclin D1 level, the greater the resistance to CDDP. This correlation allows a choice of treatment to be made. In the case where p21 protein levels were elevated the correlation was not particularly marked and was insufficient for selecting an appropriate treatment.

EXAMPLES 3 and 4

Radiosensitivity Using p53/Raf-1 and p21/Raf-1 Relationships

A number of cell lines were selected and their radiosensitivity was tested in combination with their levels of Raf-1 protein. The p53 mutational status was measured as described in Example 1. The p21 and Raf-1 levels were also measured using Western blotting according to substantially standard methods, as described above. The results for p53 mutants are shown in FIG. 4 and the corresponding results for p53 wild type cell lines are shown in FIG. 5. The results for cell lines in which p21 protein levels were not elevated (undetectable) are shown in FIG. 6, whilst the results for cell lines in which p21 protein levels were elevated are shown in FIG. 7. In p53 wild type cell lines, and in cell lines where p21 protein levels were elevated, the higher the Raf-1 level, the greater the radiosensitivity of the cells. This correlation allows a choice of treatment to be made. In p53 mutant cell lines and in cell lines where p21 protein levels were not elevated, the correlation was not particularly marked and was insufficient for selecting an appropriate treatment.

EXAMPLES 5 and 6

Choice of Taxane or Other Chemotherapeutic Agent Using p53/Cyclin D1 and p21/Cyclin D1 Relationships The experimentation that has been undertaken to measure the clonogenic cell survival of a wide range of human in vitro cell lines of different histology after exposure to taxanes is described below.

Materials and Methods
Cell Lines and Clonogenic Cell Survival Assays

The growth characteristics clonogenic assay procedures of the 11 human in vitro cell lines used in this analysis have already been reported e.g. in Britten R. A. and Warenius H., Eur. J. Canc. 29A, 1315–1320 (1993). The cell lines are listed, with their histological classification in Table 4. All are well established; many having been growing in vitro for several years. Cell lines were either donations or purchased by our laboratories. On receipt all were grown for 5 passages to provide sufficient cells for batch storage in liquid nitrogen. During this period contamination was excluded by at least one passage in antibiotic free medium and mycoplasma testing was carried out on all lines. For clonogenic assays, cells were taken from a designated primary liquid nitrogen batch and grown for 3–6 passages until there were sufficient well-growing cells. Further batches from these cells were frozen in liquid nitrogen. Cells were routinely maintained in DMEM medium. All lines were supplemented with 10% heat-inactivated foetal calf serum (HIFCS). Table 2 also shows relative values for cyclin D1 levels in five p53 mutant and six p53 wild-type human in vitro cells lines. Also shown are the absolute and relative D0.1 values (i.e. the dose of the drug that reduces the clonogenic cell survival to 10% of the untreated control cells) for CDDP and Paclitaxel (TAXOL). The D0.1 values were obtained by several independent clonogenic assays and the data fitted by linear regression analysis. The clonogenic assays were repeated until statistically satisfactory fits were achieved on linear regression.

The D0.1 values were obtained by interpolation of the linear regression lines. The cytotoxic drug D0.1 values have been normalised and expressed as relative D0.1 values, to enable the relative sensitivity of each cell to each of the drugs to be compared. In order to normalize the values, the mean D0.1 was calculated independently for CDDP and Paclitaxel (TAXOL); each absolute D0.1 value was then adjusted by dividing by the mean value to give a relative D0.1 value for each drug for each cell.

The results set out in Table 2 are plotted in the graphs shown in FIGS. 10 and 11. FIG. 10 shows relative D0.1 values for CDDP and Paclitaxel (TAXOL) in five p53 mutant cell lines. Three of the cell lines are relatively resistant to CDDP, but not to Paclitaxel (TAXOL). The remaining two cell lines which are less relatively resistant to CDDP are only slightly more sensitive to Paclitaxel (TAXOL) than to CDDP. There would thus be an advantage in using Paclitaxel (TAXOL) rather than CDDP (CISPLATIN) in the former three cell lines, but not in the latter two.

FIG. 11 shows that there is no relationship between Cyclin D1 protein levels and relative sensitivity to CDDP in wild type p53. Moreover, some cell lines are relatively more resitant to Paclitaxel (TAXOL) than CDDP. Thus, in wild-type p53 cell lines, Cyclin D1 is not a useful indicator either of resistance to CDDP or of whether the cell would preferentially respond to Paclitaxel (TAXOL) rather than CDDP.

TABLE 2

|  | Relative Cyclin D1 protein levels | CDDP | | Paclitaxel (TAXOL) | |
| --- | --- | --- | --- | --- | --- |
|  |  | Absolute D0.1 | Relative D0.1 | Absolute D0.1 | Relative D0.1 |
| p53 mutant cell lines |  |  |  |  |  |
| A431 | 3.21 (0.24)* | 0.306 | 0.765 | 0.823 | 0.292 |
| HT29 | 9.39 (1.47) | 0.632 | 1.58 | 1.106 | 0.392 |
| MOR | 8.86 (0.87) | 0.629 | 1.573 | 1.209 | 0.429 |
| RT112 | 3.19 | 0.237 | 0.593 | 1.523 | 0.540 |
| MEL2 | 7.32 | 0.457 | 1.143 | 0.57 | 0.202 |
| p53 wild-type cell lines |  |  |  |  |  |
| 2780 | 4.42 (0.06) | 0.255 | 0.637 | 2.113 | 0.749 |
| 1407 | 0.28 (0.01) | 0.06 | 0.15 | 1.504 | 0.537 |
| HRT18 | 4.44 (0.01) | 0.864 | 2.16 | 10.415 | 3.693 |
| MGHU1 | 6.23 (0.28) | 0.4494 | 1.235 | 1.144 | 0.406 |
| CORL23 | 2.11 (0.05) | 0.338 | 0.845 | 0.497 | 0.176 |
| OAW42 | 6.65 | 0.108 | 0.27 | 10.097 | 3.581 |

*(±1 S.E.M.)

The mutant p53 cell lines investigated above all showed substantially undetectable levels of p21 protein, whilst the wild-type p53 cell lines all contained detectable quantities of p21 protein. Thus, the data obtained in respect of the correlation of p21 protein and cyclin D1 levels shown in Table 3 below correspond exactly to the data in Table 2.

TABLE 3

| | | CDDP | | Paclitaxel (TAXOL) | |
|---|---|---|---|---|---|
| | Relative Cyclin D1 protein levels | Absolute D0.1 | Relative D0.1 | Absolute D0.1 | Relative D0.1 |
| Undetectable p21 | | | | | |
| A431 | 3.21 (0.24)* | 0.306 | 0.765 | 0.823 | 0.292 |
| HT29 | 9.39 (1.47) | 0.632 | 1.58 | 1.106 | 0.392 |
| MOR | 8.86 (0.87) | 0.629 | 1.573 | 1.209 | 0.429 |
| RT112 | 3.19 | 0.237 | 0.593 | 1.523 | 0.540 |
| MEL2 | 7.32 | 0.457 | 1.143 | 0.57 | 0.202 |
| Detectable p21 | | | | | |
| 2780 | 4.42 (0.06) | 0.255 | 0.637 | 2.113 | 0.749 |
| 1407 | 0.28 (0.01) | 0.06 | 0.15 | 1.504 | 0.537 |
| HRT18 | 4.44 (0.01) | 0.864 | 2.16 | 10.415 | 3.693 |
| MGHU1 | 6.23 (0.28) | 0.4494 | 1.235 | 1.144 | 0.406 |
| CORL23 | 2.11 (0.05) | 0.338 | 0.845 | 0.497 | 0.176 |
| OAW42 | 6.65 | 0.108 | 0.27 | 10.097 | 3.581 |

*(±1 S.E.M.)

The results set out in Table 3 are plotted in the graphs shown in FIGS. 12 and 13 shows relative D0.1 values for CDDP and Paclitaxel (TAXOL) in five cell lines in which p21 protein was substantially undetectable. Three of the cell lines are relatively resistant to CDDP, but not to Paclitaxel (TAXOL). The remaining two cell lines which are less relatively resistant to CDDP are only slightly more sensitive to Paclitaxel TAXOL) than to CDDP. There would thus be an advantage in using Paclitaxel (TAXOL) rather than CDDP (CISPLATIN) in the former three cell lines, but not in the latter two.

FIG. 13 shows that there is no relationship between Cyclin D1 protein levels and relative sensitivity to CDDP in cells in which p21 protein is present in detectable quantities. Moreover, some cell lines are relatively more resistant to Paclitaxel (TAXOL) than CDDP. Thus, in cell lines in which p21 protein is detectable, Cyclin D1 is not a useful indicator either of resistance to CDDP or of whether the cell would preferentially respond to (TAXOL) rather than CDDP.

The Histology of the cell lines used in the above investigations is shown below in Table 4.

TABLE 4

| | |
|---|---|
| A431 | Squamous carcinoma vulva |
| HT29 | Adenocarcinoma colon |
| MOR | Adenocarcinoma lung |
| RT112 | Transitional cell carcinoma bladder |
| MEL2 | Malignant melanoma |
| 2780 | Ovarian carcinoma |
| I407 | Embrionic intestinal epithelium |
| HRT18 | Adenocarcinoma rectum |
| MGHU1 | Transitional cell carcinoma bladder |
| CORL23 | Large cell lung carcinoma |
| OAW42 | Ovarian carcinoma |

In order to assay CDDP sensitivity $10^2$–$10^5$ cells were plated in 3 ml of Ham's F12 medium supplemented with 10% FCS in 6 well plates and incubated at 37° C. in an atmosphere of 5% $CO_2$ for 8 hours. Dilutions of 0.02–2.0 μg/ml from a 1 mg/ml stock solution of CDDP (light protected) were then made and 1 ml of the appropriate dilution were added to each plate to give a final volume of 4 ml. The plates were then incubated at 37° C. in an atmosphere of 5% $CO_2$ in darkness for 14 days in the presence of the CDDP. The medium was then removed, the cells were fixed in 70% ethanol and stained with 10% Giemsa and colonies of >100 cells counted. One six-well plate was used for each drug dilution. A minimum of 3 separate clonogenic assays with 6 points/drug dose/assay were necessary for each cell line. CDDP cell survival was determined at the 10% clonogenic cell survival level (D0.1) by interpolation of the fitted regression curve.

To measure Paclitaxel (TAXOL) sensitivity, the same protocol as described above for CDDP was employed, except an amphiphilic solubilising agent was added with the Paclitaxel (TAXOL).

References

Barraclough et al, J. Cell Physiolog 131: 393–401, 1987.
Chirgwin et al, Biochemistry 18: 5294–5299, 1979.
Maskos and Southern, Nucleic Acids Research 21, 2269–2270, 1993.
Pease et al. Proc. Natl. Acad. Sci. USA. 91, 5022–5026, 1994.
Sanger et al, Proc. Natl. Acad. Sci. USA 74: 5463–5467, 1977.
Southern et al, Nucleic Acids Research 22, 1368–1373, 1994.
Warenius et al., Int.J.Cancer. 67: 224–231, 1996.
Bristow et al., Oncogene 9: 1527–1536, 1994.
Bristow et al., Radiotherapy and Oncology 40: 197–223, 1996.
P. W. G. Browning, "Proto-oncogene expression and intrinsic radiosensitivity, PhD Thesis, University of Liverpool, 1997.
Deacon et al, Radiotherapy and Oncology 2,317–323, 1984.
Fan et al, Cancer Res. 54: 5824–5830, 1994.
Fertil & Malaise, Int. J. Radiat. Oncol. Biol. Phys. 7: 621–629, 1981.
FitzGerald et al, Radiat. Res. 122: 44–52, 1990.
Hollstein et al, Science 253: 49–53, 1991.
Iliakis et al., Cancer Res. 50: 6575–6579, 1990.
Kasid et al., Cancer Res. 49: 3396–3400, 1989.
Kastan et al, Cancer Res. 51: 6304–6311, 1991.
Kawashima et al., Int. J. Cancer 61: 76–79, 1995.
Kelland et al, Radiat. Res. 116: 526–538, 1988
Lee and Bernstein, Proc. Natl. Acad. Sci. USA 90: 5742–5746, 1993.
McIlwrath et al., Cancer Res. 54: 3718–3722, 1994.
McKenna et al., Cancer Res. 50: 97–102, 1990.
McKenna et al., Radiat. Res. 125: 283–287, 1991
Nunez et al, Br. J. Cancer 71: 311–316, 1995
Pardo et al., Radiat Res. 140: 180–185, 1994
Pirollo et al., Int. J. Radiat. Biol. 55: 783–796, 1989
Pirollo et al., Radiat. Res. 135: 234–243, 1993.
Powell & McMillan, Int. J. Rad. Oncol Biol. Phys., 29: 1035–1040, 1994.
Radford, Int. J. Radiat. Biol. 66: 557–560, 1994.
Sanger et al, Proc. Natl. Acad. Sci. USA 74: 5463–5467, 1977.
Schwartz et al., Int. J. Radiat. Biol. 59: 1314–1352, 1991.
Shimm et al., Radiat. Res. 129: 149–156, 1992.
Siles et al., Br. J. Cancer 73: 581–588, 1996.
Su & Little, Int. J. Radiat. Biol. 62: 461–468, 1992.
Su & Little, Radiat. Res. 133: 73–79, 1993.
Suzuki et al., Radiat. Res. 129: 157–162, 1992.
Warenius et al., Eur. J. Cancer 30, 369–375, 1994.
Warenius et al., Rad. Research 146,485–493, 1996.
Whitaker et al., Int. J. Radiat. Biol. 67: 7–18, 1995.
Xia et al., Cancer Res. 55: 12–15, 1995.
Zhen et al., Mut. Res. 346, 85–92, 1995.

What is claimed is:

1. A method for predicting the sensitivity of cancer cells to a chemotherapeutic agent, which method comprises:
   (a) testing a sample of said cancer cells for the expression level of a negative signal transduction factor (NSTF);
   (b) testing said sample for the expression level of a positive signal transduction factor (PSTF);
   (c) correlating said NSTF and PSTF expression levels with said sensitivity and
   (d) predicting said sensitivity of said cancer cells to said chemotherapeutic agent based on said correlation.

2. A method according to claim 1, wherein said NSTF is a factor which has an activity selected from the group consisting of inhibiting or arresting the cell cycle, causing withdrawal from the cell cycle, and/or causing apoptosis or other cell death thereby inhibiting cell division.

3. A method according to claim 1, wherein said NSTF is a suppressor of signal transduction.

4. A method according to claim 1, wherein said NSTF is selected from the group consisting of p53 and p21.

5. A method according to claim 1, wherein said NSTF is a PSTF inhibitor.

6. A method according to claim 5, wherein said PSTF inhibitor is selected from the group consisting of a Raf-1 inhibitor, a cyclin D1 inhibitor and a cyclin dependent kinase inhibitor.

7. A method according to claim 1, wherein said PSTF is a factor which has an activity selected from the group consisting of stimulating cells to enter the cell cycle, initiating and/or carrying out DNA synthesis, and controlling the passage of cells through the cell cycle.

8. A method according to claim 7, wherein said PSTF is selected from the group consisting of a transcription factor, an oncogene, a proto-oncogene, a gene which inhibits and/or controls cell cycle division, and a cell surface receptor.

9. A method according to claim 7, wherein said PSTF is selected from the group consisting of Raf-1 protein, cyclin D1 protein and a cyclin dependent kinase.

10. A method according to claim 1, wherein said chemotherapeutic agent comprises a platinating agent.

11. A method according to claim 10, wherein said platinating agent comprises CDDP.

12. A method according to claim 1, wherein said sample is extracted from a subject.

* * * * *

SEQUENCE LISTING

<160> NUMBER OF SEQ ID NOS: 15

<210> SEQ ID NO 1
<211> LENGTH: 20
<212> TYPE: DNA
<213> ORGANISM: Artificial Sequence
<220> FEATURE:
<223> OTHER INFORMATION: PCR and DNA sequencing primer for exon 2/3
      sense

<400> SEQUENCE: 1 cccactttc ctcttgcagc                                              20

<210> SEQ ID NO 2
<211> LENGTH: 20
<212> TYPE: DNA
<213> ORGANISM: Artificial Sequence
<220> FEATURE:
<223> OTHER INFORMATION: PCR and DNA sequencing primer for exon 2/3
      antisense

<400> SEQUENCE: 2
agcccaaccc ttgtccttac                                             20

<210> SEQ ID NO 3
<211> LENGTH: 20
<212> TYPE: DNA
<213> ORGANISM: Artificial Sequence
<220> FEATURE:
<223> OTHER INFORMATION: PCR and DNA sequencing primer for exon 4 sense

<400> SEQUENCE: 3
ctgctctttt cacccatcta                                             20

<210> SEQ ID NO 4
<211> LENGTH: 20
<212> TYPE: DNA
<213> ORGANISM: Artificial Sequence
<220> FEATURE:
<223> OTHER INFORMATION: PCR and DNA sequencing primer for exon 4
      antisense

<400> SEQUENCE: 4
gcattgaagt ctcatggaag                                             20

<210> SEQ ID NO 5
<211> LENGTH: 20
<212> TYPE: DNA
<213> ORGANISM: Artificial Sequence
<220> FEATURE:
<223> OTHER INFORMATION: PCR primer for exon 5 sense

<400> SEQUENCE: 5
tgttcacttg tgccctgact                                             20

<210> SEQ ID NO 6
<211> LENGTH: 20
<212> TYPE: DNA
<213> ORGANISM: Artificial Sequence
<220> FEATURE:
<223> OTHER INFORMATION: PCR and DNA sequencing primer for exon 5
      antisense

<400> SEQUENCE: 6
cagccctgtc gtctctccag                                             20

<210> SEQ ID NO 7
<211> LENGTH: 20
<212> TYPE: DNA
<213> ORGANISM: Artificial Sequence
<220> FEATURE:
<223> OTHER INFORMATION: PCR and DNA sequencing primer for exon 6 sense

<400> SEQUENCE: 7
gcctctgatt cctcactgat                    20

<210> SEQ ID NO 8
<211> LENGTH: 20
<212> TYPE: DNA
<213> ORGANISM: Artificial Sequence
<220> FEATURE:
<223> OTHER INFORMATION: PCR and DNA sequencing primer for exon 6
      antisense

<400> SEQUENCE: 8
ttaacccctc ctcccagaga                    20

<210> SEQ ID NO 9
<211> LENGTH: 20
<212> TYPE: DNA
<213> ORGANISM: Artificial Sequence
<220> FEATURE:
<223> OTHER INFORMATION: PCR and DNA sequencing primer for exon 7 sense

<400> SEQUENCE: 9
actggcctca tcttgggcct                    20

<210> SEQ ID NO 10
<211> LENGTH: 20
<212> TYPE: DNA
<213> ORGANISM: Artificial Sequence
<220> FEATURE:
<223> OTHER INFORMATION: PCR and DNA sequencing primer for exon 7
      antisense

<400> SEQUENCE: 10
tgtgcagggt ggcaagtggc                    20

<210> SEQ ID NO 11
<211> LENGTH: 15
<212> TYPE: DNA
<213> ORGANISM: Artificial Sequence
<220> FEATURE:
<223> OTHER INFORMATION: PCR and DNA sequencing primer for exon 8 sense

<400> SEQUENCE: 11
tatcctgagt agtgg                         15

<210> SEQ ID NO 12
<211> LENGTH: 15
<212> TYPE: DNA
<213> ORGANISM: Artificial Sequence
<220> FEATURE:
<223> OTHER INFORMATION: PCR and DNA sequencing primer for exon 8
      antisense

<400> SEQUENCE: 12
tgcttgctta cctcg                         15

<210> SEQ ID NO 13
<211> LENGTH: 20

-continued

```
<212> TYPE: DNA
<213> ORGANISM: Artificial Sequence
<220> FEATURE:
<223> OTHER INFORMATION: PCR and DNA sequencing primer for exon 9/10/11
      sense

<400> SEQUENCE: 13
agaaagggga gcctcaccac                                              20

<210> SEQ ID NO 14
<211> LENGTH: 20
<212> TYPE: DNA
<213> ORGANISM: Artificial Sequence
<220> FEATURE:
<223> OTHER INFORMATION: PCR and DNA sequencing primer for exon 9/10/11
      antisense

<400> SEQUENCE: 14
ctgacgcaca cctattgcaa                                              20

<210> SEQ ID NO 15
<211> LENGTH: 15
<212> TYPE: DNA
<213> ORGANISM: Artificial Sequence
<220> FEATURE:
<223> OTHER INFORMATION: DNA sequencing primer for exon 5 sense

<400> SEQUENCE: 15
tactcccctg ccctc                                                   15
```